United States Patent
Burgmeier et al.

(10) Patent No.: US 11,541,152 B2
(45) Date of Patent: Jan. 3, 2023

(54) MEDICAL DEVICE WITH DRUG-ELUTING COATING ON MODIFIED DEVICE SURFACE

(71) Applicant: Lutonix, Inc., Franklin Lakes, NJ (US)

(72) Inventors: Robert E. Burgmeier, Franklin Lakes, NJ (US); Oleg Stanilevskiy, Franklin Lakes, NJ (US); Jeffrey Wang, Franklin Lakes, NJ (US)

( * ) Notice: Subject to any disclaimer, the term of this patent is extended or adjusted under 35 U.S.C. 154(b) by 0 days.

(21) Appl. No.: 17/291,806

(22) PCT Filed: Nov. 14, 2018

(86) PCT No.: PCT/US2018/061116
§ 371 (c)(1),
(2) Date: May 6, 2021

(87) PCT Pub. No.: WO2020/101675
PCT Pub. Date: May 22, 2020

(65) Prior Publication Data
US 2021/0386917 A1    Dec. 16, 2021

(51) Int. Cl.
*A61L 29/14* (2006.01)
*A61K 31/337* (2006.01)
(Continued)

(52) U.S. Cl.
CPC .......... *A61L 29/148* (2013.01); *A61K 31/337* (2013.01); *A61L 29/085* (2013.01);
(Continued)

(58) Field of Classification Search
CPC ..... A61L 29/148; A61L 29/00; A61K 31/337; A61M 25/10; A61M 37/00
See application file for complete search history.

(56) References Cited

U.S. PATENT DOCUMENTS

| 4,316,885 A | 2/1982 | Rakhit |
| 5,023,262 A | 6/1991 | Caufield et al. |

(Continued)

FOREIGN PATENT DOCUMENTS

| WO | 0010622 A1 | 3/2000 |
| WO | 03090818 A2 | 11/2003 |

(Continued)

OTHER PUBLICATIONS

R1, Microholes, Oct. 2017, Meko Laser Material Processing, pp. 1-3 (Year: 2017).*

(Continued)

*Primary Examiner* — Dah-Wei D. Yuan
*Assistant Examiner* — Andrew J Bowman
(74) *Attorney, Agent, or Firm* — Dinsmore & Shohl

(57) ABSTRACT

Medical devices such as stents, stent grafts, and balloon catheters include a coating layer applied over a modified exterior surface of the medical device. The modified exterior surface comprises an exterior surface of the medical device subjected to a surface modification that decreases a surface free energy of the exterior surface before application of the coating layer an exterior surface. The coating layer comprises a hydrophobic therapeutic agent and at least one additive. The modified exterior surface may affect the release kinetics of the drug from the device, the crystallinity of the drug layer, the surface morphology of the coating and particle shape, or the particle size of drug of a therapeutic layer in the coating layer. For example, the effects caused by the modified exterior surface may increase the retention time and amount of therapeutic agent in tissue.

8 Claims, 3 Drawing Sheets

(51) Int. Cl.
*A61L 29/08* (2006.01)
*A61M 25/00* (2006.01)
*B05D 3/14* (2006.01)

(52) U.S. Cl.
CPC ......... *A61M 25/0009* (2013.01); *B05D 3/142* (2013.01); *A61L 2300/216* (2013.01); *A61L 2300/802* (2013.01); *A61L 2400/18* (2013.01); *A61L 2420/02* (2013.01); *A61L 2420/08* (2013.01)

(56) References Cited

U.S. PATENT DOCUMENTS

| | | | |
|---|---|---|---|
| 5,023,263 A | 6/1991 | Von Burg | |
| 5,023,264 A | 6/1991 | Caufield et al. | |
| 5,100,883 A | 3/1992 | Schiehser | |
| 5,102,876 A | 4/1992 | Caufield | |
| 5,169,851 A | 4/1992 | Hughes et al. | |
| 5,118,677 A | 6/1992 | Caufield | |
| 5,118,678 A | 6/1992 | Kao et al. | |
| 5,120,725 A | 6/1992 | Kao et al. | |
| 5,120,726 A | 6/1992 | Failli et al. | |
| 5,120,727 A | 6/1992 | Kao et al. | |
| 5,120,842 A | 6/1992 | Failli et al. | |
| 5,130,307 A | 7/1992 | Failli et al. | |
| 5,138,051 A | 8/1992 | Hughes et al. | |
| 5,151,413 A | 9/1992 | Caufield et al. | |
| 5,162,333 A | 11/1992 | Failli et al. | |
| 5,164,399 A | 11/1992 | Failli et al. | |
| 5,177,203 A | 1/1993 | Failli et al. | |
| 5,194,447 A | 3/1993 | Kao et al. | |
| 5,202,332 A | 4/1993 | Hughes et al. | |
| 5,221,740 A | 6/1993 | Hughes | |
| 5,233,036 A | 8/1993 | Hughes | |
| 5,260,299 A | 11/1993 | Failli et al. | |
| 5,260,300 A | 11/1993 | Hu | |
| 5,262,423 A | 11/1993 | Kao | |
| 5,262,424 A | 11/1993 | Kao | |
| 5,302,584 A | 4/1994 | Kao et al. | |
| 5,310,903 A | 5/1994 | Goulet et al. | |
| 5,344,833 A | 9/1994 | Hughes | |
| 5,346,893 A | 9/1994 | Failli et al. | |
| 5,358,944 A | 10/1994 | Caufield | |
| 5,362,718 A | 11/1994 | Skotnicki et al. | |
| 5,373,014 A | 12/1994 | Failli et al. | |
| 5,378,696 A | 1/1995 | Caufield | |
| 5,378,836 A | 1/1995 | Kao et al. | |
| 5,385,908 A | 1/1995 | Nelson et al. | |
| 5,385,909 A | 1/1995 | Nelson et al. | |
| 5,385,910 A | 1/1995 | Ocain et al. | |
| 5,389,639 A | 2/1995 | Failli et al. | |
| 5,391,730 A | 2/1995 | Skotnicki et al. | |
| 5,411,967 A | 5/1995 | Kao et al. | |
| 5,434,260 A | 7/1995 | Skotnicki et al. | |
| 5,440,056 A | 8/1995 | Klein et al. | |
| 5,446,048 A | 8/1995 | Failli et al. | |
| 5,463,048 A | 10/1995 | Skotnicki et al. | |
| 5,480,988 A | 1/1996 | Failli et al. | |
| 5,480,989 A | 1/1996 | Kao et al. | |
| 5,484,790 A | 1/1996 | Failli et al. | |
| 5,484,791 A | 1/1996 | Failli et al. | |
| 5,486,522 A | 1/1996 | Failli et al. | |
| 5,486,523 A | 1/1996 | Failli et al. | |
| 5,486,524 A | 1/1996 | Failli et al. | |
| 5,488,054 A | 1/1996 | Failli et al. | |
| 5,489,595 A | 2/1996 | Failli et al. | |
| 5,489,680 A | 2/1996 | Failli et al. | |
| 5,491,231 A | 2/1996 | Nelson et al. | |
| 5,504,091 A | 4/1996 | Molnar-Kimber et al. | |
| 5,504,204 A | 4/1996 | Failli et al. | |
| 5,504,291 A | 4/1996 | Goble et al. | |
| 5,508,285 A | 4/1996 | Nelson et al. | |
| 5,508,286 A | 4/1996 | Skotnicki et al. | |
| 5,508,290 A | 4/1996 | Nelson et al. | |
| 5,508,399 A | 4/1996 | Kao et al. | |
| 5,516,780 A | 5/1996 | Skotnicki et al. | |
| 5,519,031 A | 5/1996 | Skotnicki et al. | |
| 5,521,194 A | 5/1996 | Nelson et al. | |
| 5,525,610 A | 6/1996 | Caufield et al. | |
| 5,530,007 A | 6/1996 | Kao et al. | |
| 5,530,121 A | 6/1996 | Kao et al. | |
| 5,532,355 A | 7/1996 | Skotnicki et al. | |
| 5,541,191 A | 7/1996 | Skotnicki et al. | |
| 5,541,192 A | 7/1996 | Skotnicki et al. | |
| 5,550,133 A | 8/1996 | Failli et al. | |
| 5,559,112 A | 9/1996 | Skotnicki et al. | |
| 5,559,119 A | 9/1996 | Skotnicki et al. | |
| 5,559,120 A | 9/1996 | Kao et al. | |
| 5,559,122 A | 9/1996 | Nelson et al. | |
| 5,563,145 A | 10/1996 | Failli et al. | |
| 5,567,709 A | 10/1996 | Skotnicki et al. | |
| 5,637,590 A | 6/1997 | Skotnicki et al. | |
| 5,665,772 A | 9/1997 | Cottens et al. | |
| 5,780,462 A | 7/1998 | Lee et al. | |
| 5,868,704 A * | 2/1999 | Campbell | A61F 2/958 604/103.11 |
| 5,912,253 A | 6/1999 | Cottens et al. | |
| 5,922,730 A | 7/1999 | Hu et al. | |
| 5,955,457 A | 9/1999 | Lee et al. | |
| 5,985,890 A | 11/1999 | Cottens et al. | |
| 6,004,973 A | 12/1999 | Guitard et al. | |
| 6,015,809 A | 1/2000 | Zhu et al. | |
| 6,200,985 B1 | 3/2001 | Cottens et al. | |
| RE37,421 E | 10/2001 | Holt et al. | |
| 6,329,386 B1 | 12/2001 | Mollison | |
| 6,399,625 B1 | 6/2002 | Zhu | |
| 6,440,990 B1 | 8/2002 | Cottens et al. | |
| 6,677,357 B2 | 1/2004 | Zhu et al. | |
| 6,680,330 B2 | 1/2004 | Zhu et al. | |
| 7,160,867 B2 | 1/2007 | Abel et al. | |
| 7,220,755 B2 | 5/2007 | Betts et al. | |
| 7,241,771 B2 | 7/2007 | Zhu | |
| 7,268,144 B2 | 9/2007 | Gu et al. | |
| 7,273,874 B2 | 9/2007 | Graziani et al. | |
| 7,279,562 B2 | 10/2007 | Molnar-Kimber et al. | |
| 7,282,505 B2 | 10/2007 | Zhu et al. | |
| 7,445,916 B2 | 11/2008 | Gu et al. | |
| 7,446,111 B2 | 11/2008 | Benjamin et al. | |
| 7,455,853 B2 | 11/2008 | Mollison et al. | |
| 7,470,682 B2 | 12/2008 | Graziani et al. | |
| 7,476,678 B2 | 1/2009 | Graziani et al. | |
| 7,538,119 B2 | 5/2009 | Gu et al. | |
| 7,560,457 B2 | 7/2009 | Graziani et al. | |
| 8,244,344 B2 * | 8/2012 | Wang | A61L 31/08 604/509 |
| 2004/0010002 A1 | 1/2004 | Wasik et al. | |
| 2005/0271700 A1 | 12/2005 | DesNoyer et al. | |
| 2006/0264453 A1 | 11/2006 | Mudumba et al. | |
| 2007/0142423 A1 | 6/2007 | Graziani et al. | |
| 2007/0190103 A1 | 8/2007 | Hossainy et al. | |
| 2007/0203168 A1 | 8/2007 | Zhao | |
| 2007/0203169 A1 | 8/2007 | Zhao | |
| 2007/0203170 A1 | 8/2007 | Zhao | |
| 2007/0203171 A1 | 8/2007 | Zhao | |
| 2007/0203172 A1 | 8/2007 | Zhao | |
| 2007/0212394 A1 | 9/2007 | Reyes et al. | |
| 2007/0225313 A1 | 9/2007 | Zhao | |
| 2007/0280992 A1 | 12/2007 | Margaron et al. | |
| 2008/0069797 A1 | 3/2008 | Roncarolo et al. | |
| 2008/0085880 A1 | 4/2008 | Viswanath et al. | |
| 2008/0091008 A1 | 4/2008 | Viswanath et al. | |
| 2008/0171087 A1 | 7/2008 | Chappa et al. | |
| 2008/0182867 A9 | 7/2008 | Wasik et al. | |
| 2008/0188511 A1 | 8/2008 | Beckmann et al. | |

(56) References Cited

U.S. PATENT DOCUMENTS

2008/0249123 A1 10/2008 Gu et al.
2017/0014601 A1* 1/2017 Kurosaki .............. A61L 29/085

FOREIGN PATENT DOCUMENTS

WO  2007094940 A2  8/2007
WO  2008022258 A2  2/2008

OTHER PUBLICATIONS

Xi et al., Super Hydrophobic Parylene-C Produced by Consecutive O2 and SF6 Plasma Treatment, Jun. 2014, Journal of Microelectromechanical Systems, vol. 23, No. 3, pp. 628-635 (Year: 2014).*
The International Search Report and Written Opinion dated Jul. 23, 2019 in corresponding PCT International Patent Application No. PCT/US2018/061116.
Office Action dated Mar. 31, 2022, pertaining to Chinese Patent Application No. 201880100442.X.
Office Action dated Oct. 6, 2022, pertaining to JP application 2021-526510.

* cited by examiner

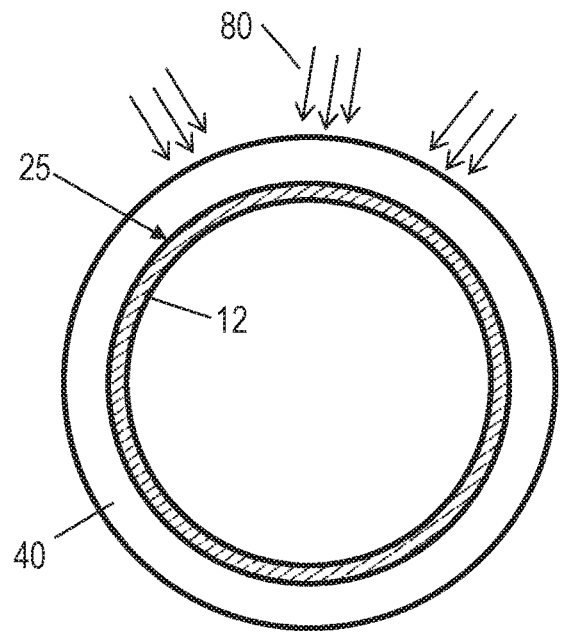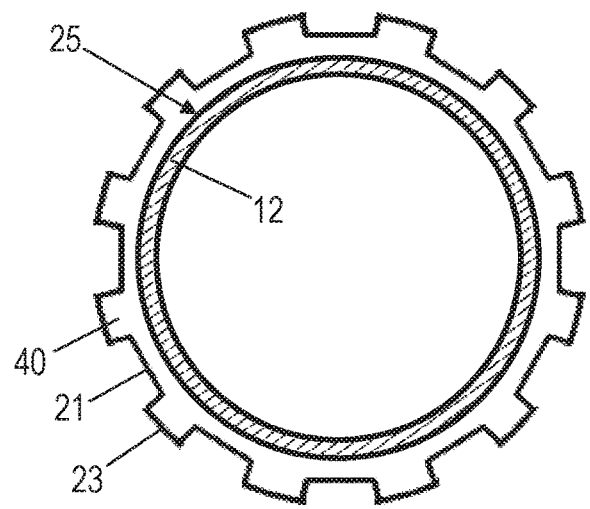
FIG. 3A    FIG. 3B
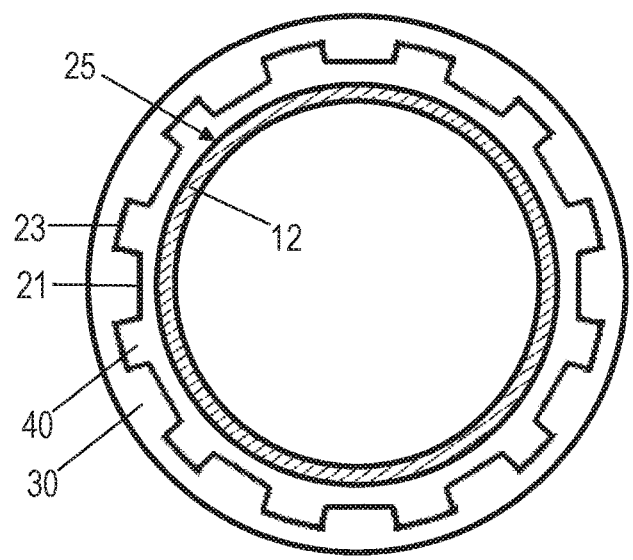
FIG. 3C

MEDICAL DEVICE WITH DRUG-ELUTING COATING ON MODIFIED DEVICE SURFACE

FIELD

Embodiments of the present disclosure relate to coated medical devices, and particularly to coated balloon catheters, and their use for rapidly and efficiently/effectively delivering a therapeutic agent to particular tissue or body lumen, for treatment of disease and particularly for reducing stenosis and late lumen loss of a body lumen. Embodiments of the present disclosure also relate to methods of manufacturing these medical devices, the coatings provided on these medical devices, and to methods for treating a body lumen such as the vasculature, including particularly arterial, venous, or arteriovenous vasculature, for example, using these coated medical devices.

BACKGROUND

It has become increasingly common to treat a variety of medical conditions by introducing a medical device into the vascular system or other lumen within a human or veterinary patient such as the esophagus, trachea, colon, biliary tract, sinus passages, nasal passages, renal arteries, or urinary tract. For example, medical devices used for the treatment of vascular disease include stents, catheters, balloon catheters, guide wires, cannulas and the like. While these medical devices initially appear successful, the benefits are often compromised by the occurrence of complications, such as late thrombosis, or recurrence of disease, such as stenosis (restenosis), after such treatment.

Combining drugs and medical devices is a complicated area of technology. It involves the usual formulation challenges, such as those of oral or injectable pharmaceuticals, together with the added challenge of maintaining drug adherence to the medical device until it reaches the target site and subsequently delivering the drug to the target tissues with the desired release and absorption kinetics. Furthermore, coatings must not impair functional performance such as burst pressure and compliance of balloons. The coating thickness must also be kept to a minimum, since a thick coating would increase the medical device's profile and lead to poor trackability and deliverability. These coatings generally contain almost no liquid chemicals, which typically are often used to stabilize drugs. Thus, formulations that are effective with pills or injectables might not work at all with coatings of medical device. If the drug releases from the device too easily, it may be lost during device delivery before it can be deployed at the target site, or it may burst off the device during the initial phase of inflation and wash away before being pressed into contact with target tissue of a body lumen wall. If the drug adheres too strongly, the device may be withdrawn before the drug can be released and absorbed by tissues at the target tissues.

In some instances, functional layers may be applied to medical devices such as balloon catheters for the purpose of increasing adhesion of a drug-containing layer to a balloon catheter. However, an increase of adhesion may be expected to adversely affect the uptake of the drug into the target site being treated or the long-term efficacy of the drug at the target site at least 14 days or at least 28 days post-treatment.

Thus, there is still a need to develop highly specialized coatings for medical devices that can effectively/efficiently and rapidly deliver therapeutic agents, drugs, or bioactive materials directly into a localized tissue area during or following a medical procedure, so as to treat or prevent vascular and nonvascular diseases such as restenosis. The device should quickly release the therapeutic agent in an effective and efficient manner at the desired target location, where the therapeutic agent should rapidly permeate the target tissue to treat disease, for example, to relieve stenosis and prevent restenosis and late lumen loss of a body lumen. Furthermore, it is also desirable that concentration of the therapeutic agent remain elevated at the target site at least 14 days or at least 28 days post-treatment, so as to maintain the therapeutic effects of the therapeutic agent.

SUMMARY

Except where stated otherwise, all molecular weights herein are reported in Daltons (g/mol). Molecular weights of polymeric materials are reported as weight-average molecular weights.

Embodiments of the present disclosure relate to medical devices, including particularly balloon catheters and stents, for which an exterior surface of the medical device is subjected to a surface modification to lower the surface free energy of the exterior surface before a drug-releasing coating is applied over the exterior surface. Further embodiments include methods for preparing the medical devices. An object of embodiments of the present disclosure is to facilitate rapid and efficient uptake of drug by target tissue during transitory device deployment at a target site. A further object of embodiments of the present disclosure is to maintain or increase long-term efficacy of drug up to 14 days or 28 days post-treatment.

Embodiments of this disclosure include medical devices including a coating layer applied over a modified exterior surface of the medical device. The modified exterior surface includes an exterior surface of the medical device that has been subjected to a surface modification that decreases a surface free energy of the exterior surface before application of the coating layer. The coating layer includes a hydrophobic therapeutic agent and at least one additive. The surface modification may include, for example, a fluorine plasma treatment that implants a fluorine-containing species into the exterior surface. The surface modification may include, for example, a plasma-polymerization of an intermediate layer on the exterior surface, whereby the coating layer overlies the intermediate layer. The modified exterior surface may further include a plurality of depots etched into such a plasma-polymerized intermediate layer. When the depots are present, the coating layer may fill at least a portion of the depots.

In some nonlimiting specific embodiments, the medical device is a balloon catheter having an expandable inflatable balloon including a coating layer applied over a modified exterior surface of the balloon. The modified exterior surface includes an exterior surface of the balloon that has been subjected to a surface modification that decreases a surface free energy of the exterior surface before application of the coating layer. The balloon may include an intermediate layer comprising a polymer formed by plasma polymerization of a cycloaliphatic monomer or an aromatic monomer over the balloon. The coating layer comprises a hydrophobic therapeutic agent and at least one additive. The surface modification may include, for example, a fluorine plasma treatment that implants a fluorine-containing species into the exterior surface of the balloon. The surface modification may include, for example, a plasma-polymerization of an intermediate layer on the exterior surface, whereby the coating layer overlies the intermediate layer. The modified exterior surface may further include a plurality of depots etched into such a plasma-polymerized intermediate layer. When the depots are present, the coating layer may fill at least a portion of the depots. A drug-containing coating layer may overlie the intermediate layer. The coating layer may include a therapeutic agent and at least one additive. The coating layer may include a therapeutic agent and two or more than two additives. In some embodiments, the intermediate layer may include at least one additive. The therapeutic agent may be a hydrophobic drug. The additive or additives may include both a hydrophilic part and a drug affinity part. The drug affinity part is a hydrophobic part and/or has an affinity to the therapeutic agent by hydrogen bonding and/or van der Waals interactions.

As will be discussed in greater detail, the medical devices according to embodiments, including the modified exterior surface, exhibit unexpected therapeutic benefits beyond what has been recognized previously for medical devices that include a drug-containing layer applied to an exterior surface of a device without the surface modifications described herein. For example, the combination of the modified exterior surface and the drug containing layer in coated medical devices according to embodiments herein, such as balloon catheters, for example, may exhibit increased initial uptake of therapeutic agent and increased long-term efficacy at least 14 days or at least 28 days, despite similar amounts of residual therapeutic agent on the device post-treatment.

BRIEF DESCRIPTION OF THE DRAWINGS

FIG. 3A is a cross section of a balloon of the balloon catheter of FIG. 1, taken along line A-A, including an intermediate layer, prior to an etching procedure according to embodiments.

FIG. 3B is the cross section of FIG. 3A, including the intermediate layer after the etching procedure according to embodiments.

FIG. 3C is the cross section of FIG. 3B, after application of a drug coating layer over the etched intermediate layer according to embodiments.

DETAILED DESCRIPTION

As used herein, the interchangeable terms "coating" and "layer" refer to material that is applied, or that has been applied, onto a surface or a portion of a surface of a substrate using any customary application or deposition method such as vapor deposition, spray coating, dip coating, painting, spin coating, sputtering, immersion coating, plasma-assisted deposition, or vacuum evaporation, for example.

The terms "coated" and "applied" as verbs may be used interchangeably herein. Except where stated otherwise, a reference to a "substrate coated with a certain material" or the like is equivalent to a "substrate to which a certain material has been applied" to a surface or a portion of a surface of the substrate using any customary application or deposition method such as vapor deposition, spray coating, dip coating, painting, spin coating, sputtering, immersion coating, plasma-assisted deposition, or vacuum evaporation, for example.

Medical Device

Embodiments of medical devices, including as non-limiting examples balloon catheters and stents will now be described. In the medical devices, an exterior surface of the medical device is subjected to a surface modification to lower the surface free energy of the exterior surface before a drug-releasing coating is applied over the exterior surface. Embodiments of methods for preparing the medical devices will be described subsequently.

In some embodiments, the medical device is a balloon catheter. Referring to the example embodiment of FIG. 1, a balloon catheter 10 has a proximal end 18 and a distal end 20. The balloon catheter 10 may be any suitable catheter for desired use, including conventional balloon catheters known to one of ordinary skill in the art. For example, the balloon catheter 10 may be a rapid exchange or over-the-wire catheter. In some specific examples, the balloon catheter may be a Clear Stream™ Peripheral catheter available from BARD Peripheral Vascular. The balloon catheter 10 may be made of any suitable biocompatible material. The balloon 12 of the balloon catheter may include a polymer material, such as, for example only, polyvinyl chloride (PVC), polyethylene terephthalate (PET), polyethylene, Nylon, PEBAX (i.e. a copolymer of polyether and polyamide), polyurethane, polystyrene (PS), polyethleneterephthalate (PETP), or various other suitable materials as will be apparent to those of ordinary skill in the art.

Figure 1:
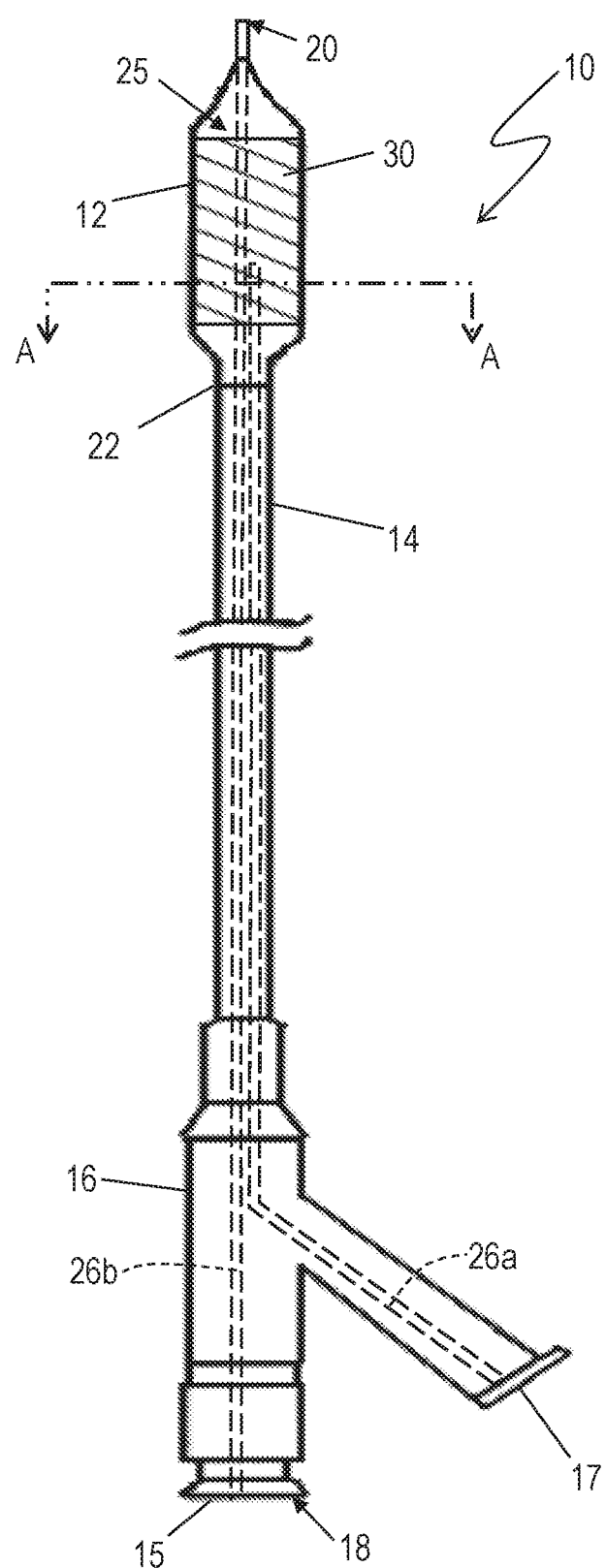
FIG. 1 is a schematic of an exemplary embodiment of a medical device, particularly a balloon catheter, according to the present disclosure.
Figure 2A:
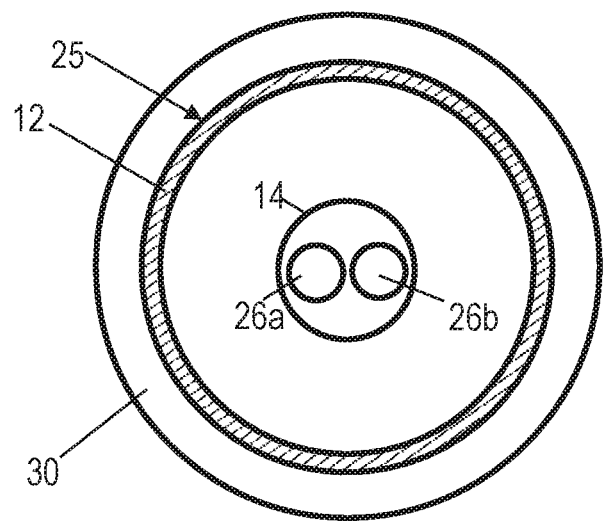
FIG. 2A is a cross-section of some embodiments of the distal portion of the balloon catheter of FIG. 1, taken along line A-A, including a drug coating layer on a modified exterior surface of a balloon.
Figure 2B:
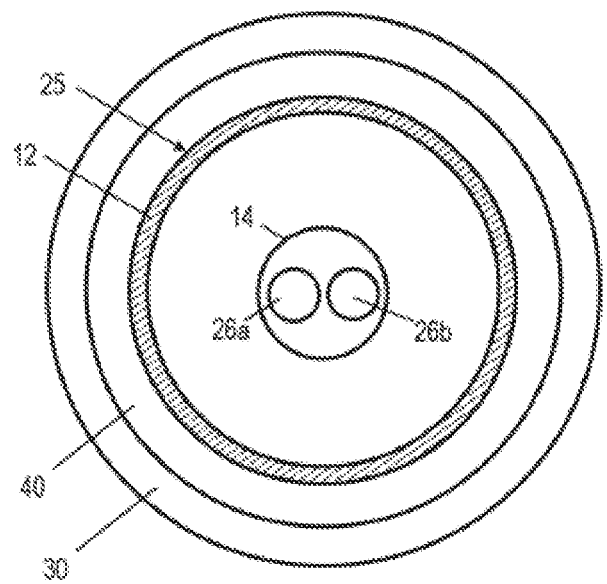
FIG. 2B and is a cross-section of some embodiments of the distal portion of the balloon catheter of FIG. 1, taken along line A-A, including an intermediate layer between a modified exterior surface of the balloon and a drug coating layer.

Various embodiments of the balloon catheter 10 of FIG. 1 are illustrated through the cross sections along line A-A of FIG. 1 in FIGS. 2A and 2B. Referring jointly to FIGS. 1, 2A, and 2B, the balloon catheter 10 includes an expandable balloon 12 and an elongate member 14. The elongate member 14 extends between the proximal end 18 and the distal end 20 of the balloon catheter 10. The elongate member 14 has at least one lumen 26a, 26b and a distal end 20. The elongate member 14 may be a flexible member which is a tube made of suitable biocompatible material. The elongate member 14 may have one lumen or, as shown in FIGS. 1, 2A, and 2B, more than one lumen 26a, 26b therein. For example, the elongate member 14 may include a guide-wire lumen 26b that extends to the distal end 20 of the balloon catheter 10 from a guide-wire port 15 at the proximal end 18 of the balloon catheter 10. The elongate member 14 may also include an inflation lumen 26a that extends from an inflation port 17 of the balloon catheter 10 to the inside of the expandable balloon 12 to enable inflation of the expandable balloon 12. From the embodiments of FIGS. 1, 2A, and 2B, even though the inflation lumen 26a and the guide-wire lumen 26b are shown as side-by-side lumens, it should be understood that the one or more lumens present in the elongate member 14 may be configured in any manner suited to the intended purposes of the lumens including, for example, introducing inflation media and/or introducing a guide-wire. Many such configurations are well known in the art.

The expandable balloon 12 is attached to the distal attachment end 22 of the elongate member 14. The expandable balloon 12 has an exterior surface 25 and is inflatable. The expandable balloon 12 is in fluidic communication with a lumen of the elongate member 14, (for example, with the inflation lumen 26a). At least one lumen of the elongate member 14 is configured to receive inflation media and to pass such media to the expandable balloon 12 for its expansion. Examples of inflation media include air, saline, and contrast media.

Still referring to FIG. 1, in one embodiment, the balloon catheter 10 includes a handle assembly such as a hub 16. The hub 16 may be attached to the balloon catheter 10 at the proximal end 18 of the balloon catheter 10. The hub 16 may connect to and/or receive one or more suitable medical devices, such as a source of inflation media (e.g., air, saline, or contrast media) or a guide wire. For example, a source of inflation media (not shown) may connect to the inflation port 17 of the hub 16 (for example, through the inflation lumen 26*a*), and a guide wire (not shown) may be introduced to the guide-wire port 15 of the hub 16, (for example through the guide-wire lumen 26*b*).

In some example embodiments, the cross section A-A of FIG. 1 may be as depicted according to FIG. 2A, in which the drug coating layer 30 is applied directly onto a modified exterior surface 25 of the balloon 12. In other example embodiments, the cross section A-A of FIG. 1 may be as depicted according to FIG. 2B, in which the drug coating layer 30 is applied onto an intermediate layer 40 overlying the modified exterior surface 25 of the balloon 12. The general mechanical structures according to these embodiments will now be described. The modified exterior surface 25 and processes included for subjecting an exterior surface to surface modification will be described in greater detail in a later section, as will the specific compositions of the drug coating layer 30 itself, according to various embodiments.

In embodiments in which the cross section A-A of FIG. 1 is as depicted according to FIG. 2A, the balloon catheter 10 includes a drug coating layer 30 applied over a modified exterior surface 25 of the balloon 12. The modified exterior surface 25 is a surface that has been subjected to a surface modification that decreases a surface free energy of the exterior surface 25 before application of the drug coating layer 30. The surface modification may include a fluorine plasma treatment that implants a fluorine-containing species into the exterior surface 25. In this regard, the drug coating layer 30 overlies a modified exterior surface 25 that may be characterized as a balloon material into which a fluorine-containing species has been implanted before the drug coating layer 30 is applied. The drug coating layer 30 itself includes a hydrophobic therapeutic agent and a combination of additives. In one particular embodiment, the drug coating layer 30 consists essentially of the hydrophobic therapeutic agent and the combination of additives. Stated another way, in this particular embodiment, the drug coating layer 30 includes only the therapeutic agent and the combination of additives, without any other materially significant components.

In embodiments in which the cross section A-A of FIG. 1 is as depicted according to FIG. 2B, the balloon catheter 10 includes a drug coating layer 30 applied over a modified exterior surface 25 of the balloon 12. The modified exterior surface 25 is a surface that has been subjected to a surface modification that decreases a surface free energy of the exterior surface 25 before application of the drug coating layer 30. The surface modification may include a plasma-polymerization of an intermediate layer on the exterior surface before the drug coating layer 30 is applied, whereby the coating layer overlies the intermediate layer 40.

In some embodiments, the surface modification optionally may include a fluorine plasma treatment that implants a fluorine-containing species directly into the exterior surface 25 before the intermediate layer 40 is applied. In this regard, the intermediate layer 40 and the drug coating layer 30 both overlie a modified exterior surface 25 that may be characterized as a balloon material into which a fluorine-containing species has been implanted. The drug coating layer 30 itself includes a hydrophobic therapeutic agent and a combination of additives. In one particular embodiment, the drug coating layer 30 consists essentially of the hydrophobic therapeutic agent and the combination of additives. Stated another way, in this particular embodiment, the drug coating layer 30 includes only the therapeutic agent and the combination of additives, without any other materially significant components. In another particular embodiment, the drug coating layer 30 is from about 0.1 μm to 15 μm thick. In embodiments the intermediate layer 40 includes a polymeric material formed by plasma polymerization of a cycloaliphatic monomer or an aromatic monomer. Examples of cycloaliphatic monomers include alkylcyclohexanes such as methylcyclohexane. Examples of aromatic monomers include alkylbenzenes such as toluene and xylenes. In some embodiments, the intermediate layer 40 comprises or consists of a poly(p-xylylene).

Without intent to be bound by theory, it is believed that application of the drug coating layer 30 onto a modified exterior surface of the balloon 12, particularly a modified exterior surface formed by subjecting the exterior surface to a surface modification that decreases the surface free energy of the exterior surface before application of the coating layer, may affect the release kinetics of drug in the coating layer from the balloon, the crystallinity of the drug layer, the surface morphology of the coating and particle shape, or the particle size of drug of a therapeutic layer in the coating layer, drug distribution on the surface. For example, the effects caused by the modified exterior surface may increase the retention time and amount of therapeutic agent in tissue, even 14 days, 21 days, or longer, after the medical device has been removed from a lumen.

In embodiments, the concentration density of the at least one therapeutic agent in the drug coating layer 30 may be from about 1 to 20 μg/mm$^2$, or more preferably from about 2 to 6 μg/mm$^2$. The ratio by weight of therapeutic agent to the additive in the coating layer may be from about 0.5 to 100, for example, from about 0.1 to 5, from 0.5 to 3, and further for example, from about 0.8 to 1.2. If the ratio (by weight) of the therapeutic agent to the additive is too low, then drug may release prematurely, and if the ratio is too high, then drug may not elute quickly enough or be absorbed by tissue when deployed at the target site. For example, a high ratio may lead to a faster release and a low ratio may lead to a slower release. Without being bound by the theory, it is believed that the therapeutic agent may release from the surface of the medical device with a larger amount of additives where the additives are water soluble.

In example embodiments, the drug coating layer 30 includes a therapeutic agent and an additive, wherein the therapeutic agent is paclitaxel and analogues thereof or rapamycin and analogues thereof, and the additive is chosen from sorbitol, diethylene glycol, triethylene glycol, tetraethylene glycol, xylitol, 2-ethoxyethanol, sugars, galactose, glucose, mannose, xylose, sucrose, lactose, maltose, Tween 20, Tween 40, Tween 60, and their derivatives, wherein the ratio by weight of the therapeutic agent to the additive is from 0.5 to 3. If the ratio of drug to additive is below 0.5, then drug may release prematurely, and if ratio is above 3, then drug may not elute quickly enough or be absorbed by tissue when deployed at the target site. In other embodiments, the drug coating layer may include a therapeutic agent and more than one additive. For example, one additive may serve to improve balloon adhesion of another additive or additives that are superior at promoting drug release or tissue uptake of drug.

In other embodiments, two or more therapeutic agents are used in combination in the drug coating layer. In other embodiments, the device may include a top layer (not shown) overlying the drug coating layer 30.

Many embodiments of the present disclosure are particularly useful for treating vascular disease and for reducing stenosis and late luminal loss, or are useful in the manufacture of devices for that purpose or in methods of treating that disease. Though embodiments have been described only with respect to balloon catheters, it should be understood that, in addition to balloon catheters, other medical devices, particularly other expandable medical devices, may be coated with a drug-containing coating layer that is applied over a modified exterior surface, such as described previously with respect to balloon catheters. Such other medical devices include, without limitation, stents, scoring balloon catheters, and recanalization catheters.

Surface Modification by Plasma Fluorination of Exterior Surface

As previously described, the medical device such as a balloon catheter 10, for example, includes a modified exterior surface 25, namely, a surface that has been subjected to a surface modification that decreases a surface free energy of the exterior surface 25 before application of the drug coating layer 30. The surface modification may include a fluorine plasma treatment, such as plasma fluorination, that implants a fluorine-containing species into the exterior surface 25 before the drug coating layer 30 is applied.

In exemplary use, at least a portion of the balloon catheter 10 is positioned within a plasma chamber for treatment by plasma fluorination. For example, the balloon 12 may be positioned within the plasma chamber such that the exterior surface 25 of the balloon 12 is treated. Although the treatment of the balloon 12 is described in the present example, it should be understood that other various portions of the balloon catheter 10 and/or other suitable medical devices may be treated by plasma fluorination. With balloon 12 positioned in the plasma chamber, a vacuum may be generated within the plasma chamber, thereby subjecting the exterior surface 25 of the balloon 12 to the vacuum atmosphere.

With the vacuum maintained within the plasma chamber, the polymer material of exterior surface 25 is exposed to a fluorine-containing species such as produced by excited fluorine or a fluorocarbon gas mixture to a plasma state. The fluorine source may be supplied by a gas source coupled to the plasma chamber. The gas source generates fluorine-containing ions (i.e. fluorinated ions) and radicals from the fluorine or fluorocarbon gas transmitted into the chamber. By way of example only, gases that may be transmitted by the gas source may include tetrafluoromethane ($CF_4$), hexafluoroethane ($C_2F_6$), xenon difluoride ($XeF_2$), fluorine ($F_2$), chloropentafluoroethane ($CF_3CClF_2$), sulfur hexafluoride ($SF_6$), and other suitable fluorine-containing gases as will be apparent to those of ordinary skill in the art. The discharge of the mixture into the chamber subjects the exterior surface 25 of the balloon 12 to the gas at a predetermined flow and for a predetermined duration.

A plasma generator in fluidic communication with the plasma chamber is then activated to discharge plasma into the plasma chamber and expose the exterior surface 25 of the balloon 12 to the plasma. As illustrative examples, the plasma generator may comprise an arc discharger, a dielectric barrier discharger, a spark discharger, resistive barrier dischargers, radio-frequency excitation, microwave frequency excitation, and other suitable generators as will be apparent to those of ordinary skill in the art.

The exterior surface 25 of the balloon 12 is fluorinated with the plasma sourced from the plasma generator when the plasma interacts with the polymer material of the exterior surface 25 at a predetermined flow. In the present example, the generated plasma comprises fluorine-containing ions and radicals. The fluorination may occur through implantation of fluorine-containing ions into the exterior surface 25. Ion implantation may include initially extracting fluorine-containing ions from the plasma generator and subsequently selecting desired ions for transmission through an accelerating column via a magnetic field of the plasma generator. In this instance, the fluorine-containing ions selected by the magnetic field are forced into the polymer material of the exterior surface 25 such that the ions are implanted into the balloon 12. Hydrogen atoms of the polymer material of the exterior surface 25 may be simultaneously replaced by the fluorine-containing species implanted into the exterior surface 25.

The portion of the balloon catheter 10 within the plasma chamber (e.g., the exterior surface 25 of the balloon 12) may be continuously treated with the plasma for a predetermined duration, thereby creating the modified exterior surface 25 along the balloon 12 having a surface free energy less than that of the exterior surface before the plasma fluorination. In some embodiments, the exterior surface 25 of the balloon 12 may be fluorinated with the plasma, thereby creating the modified exterior surface 25 along the balloon 12. In some embodiments, the plasma treatment of the modified exterior surface 25 may be applied directly on the exterior surface of balloon 12 of a fully assembled balloon catheter 10. In some embodiments, the plasma treatment 5 may be applied to a balloon material or a component including the balloon material, then the balloon material or component including the balloon material having the modified exterior surface 25 thereon may be used in assembling the balloon catheter 10. In some embodiments in which the medical device is a balloon catheter, the modified exterior surface 25 may cover the entire exterior surface of the balloon of the balloon catheter.

The modified exterior surface 25 produced by plasma fluorination thus includes a concentration of fluorine down to a particular depth into the balloon material. The fluorine concentration in the modified exterior surface 25 may have a substantially uniform distribution along the surface area of balloon 12. In some embodiments, the fluorine may penetrate into the balloon material to a depth of about 0.1 µm, 0.2 µm, 0.5 µm, 0.7 µm, or 1.0 µm, for example. As should be understood in view of the teachings herein, optimal results may be achieved during the plasma fluorination through applying appropriate gas types, gas flow, treatment times, and generator power.

Without intent to be bound by theory, it is believed that the plasma fluorination as a surface modification of the exterior surface 25 of the balloon 12 may decrease the surface free energy of the balloon material, particularly the exterior surface of the balloon material. Further, it is believed that reduction of the surface free energy of the exterior surface 25 prior to the application of the drug coating layer 30 onto the balloon 12 may modify the material properties of the exterior surface 25 to thereby provide improved interactions between the drug coating layer 30 and the balloon 12. For example, surface modification including plasma fluorination according to embodiments may facilitate uniform distribution of the drug coating layer 30 over the exterior surface 25 when the drug coating layer 30 applied. Further, the plasma fluorination of the exterior surface 25 may enhance the drug delivery and eluting characteristics of the balloon catheter 10, and further may modify the crystallinity of the drug coating layer 30 as the drug coating layer 30 is maintained on the balloon catheter 10. The decreased surface free energy attained by the plasma fluorination may increase the amount of therapeutic agent (e.g., paclitaxel, sirolimus, etc.) delivered to tissue and the retention time within the tissue after the balloon catheter 10 has been removed from the target treatment site.

The surface modification by plasma fluorination may provide benefits to the coated balloon catheter 10, particularly in the delivery of a therapeutic agent contained in the drug coating layer 30, the uptake of drug at a target site being treated, or both. The fluorine plasma treatment to the polymer material of the exterior surface 25 of the balloon 12 may affect the release kinetics of the drug from the balloon 12. The surface modification by plasma fluorination may modify the balloon surface properties, but in some embodiments, the balloon 12 may maintain its bulk properties. As a result, the surface modification by plasma fluorination may not impact the burst pressure, the compliance, or other performance properties of the balloon 12.

Intermediate Layer

When the exterior surface of the medical device is modified according to embodiments to include an intermediate layer 40, the intermediate layer 40 overlies the exterior surface 25 of the medical device. In some embodiments, the intermediate layer 40 is in direct contact with the exterior surface 25 of the medical device or is coated or applied directly onto the exterior surface 25 of the medical device. In some embodiments, the intermediate layer 40 is formed by surface chemistry applied to the exterior surface 25 of the medical device and thereby functions an integral component of the material of the medical device. In some embodiments, the medical device is a balloon catheter 10 and the intermediate layer 40 overlies an exterior surface of a balloon 12 of the balloon catheter 10. In some embodiments, the medical device is a balloon catheter 10, and the intermediate layer 40 is in direct contact with or is applied directly onto the exterior surface 25 of a balloon of the balloon catheter 10. In some embodiments, the intermediate layer 40 is formed on the exterior surface 25 of the balloon by surface chemistry applied to the exterior surface of the balloon and thereby functions an integral component of the balloon material.

The intermediate layer 40 underlies the drug coating layer 30. In some embodiments, the intermediate layer 40 may be applied directly on the exterior surface of the balloon of a fully assembled balloon catheter 10. In some embodiments, the intermediate layer 40 may be applied to a balloon material or a component including the balloon material, then the balloon material or component including the balloon material having the intermediate layer 40 thereon may be used in assembling the balloon catheter 10. In some embodiments in which the medical device is a balloon catheter, the intermediate layer 40 may cover the entire exterior surface of the balloon of the balloon catheter. In some embodiments, the intermediate layer 40 may be from 0.001 μm to 2 μm thick, or from 0.01 μm to 1 μm thick, or from 0.02 μm to 0.25 μm, or from 0.05 μm to 0.5 μm thick, or from about 0.1 μm to about 0.2 μm thick, for example.

As previously described, the intermediate layer 40 may include a polymer or an additive or mixtures of both. Particularly suitable polymers of the intermediate layer 40 include biocompatible polymers that avoid undesirable irritation of body tissue. Example polymers include polymers formed from cycloaliphatic monomers or aromatic monomers. Examples of cycloaliphatic monomers include alkyl-cyclohexanes such as methylcyclohexane. Examples of aromatic monomers include alkylbenzenes such as toluene and xylenes. In some embodiments, the intermediate layer may be a poly(p-xylylene) such as parylene C, parylene N, parylene D, parylene X, parylene AF-4, parylene SF, parylene HT, parylene VT-4 (parylene F), parylene CF, parylene A, or parylene AM, for example. Structures of selected parylenes are provided below:

Additional polymers may be present in the intermediate layer 40. Examples of such additional polymers include, for example, polyolefins, polyisobutylene, ethylene-α-olefin copolymers, acrylic polymers and copolymers, polyvinyl chloride, polyvinyl methyl ether, polyvinylidene fluoride and polyvinylidene chloride, polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, and mixtures and block copolymers thereof. In embodiments, the additional polymers may be chosen from polymers having a low surface free-energy.

Without intent to be bound by theory, it is believed that intermediate layers including certain polymer materials such as parylenes, for example, decrease the surface free-energy of the exterior surface of the balloon and thereby contribute to the benefits described herein of modifying the exterior surface of the medical device before applying the drug coating layer.

Because the medical devices according to embodiments, particularly balloon catheters and stents, for example, undergo mechanical manipulation, i.e., expansion and contraction, further examples of polymers that are useful in the intermediate layer include elastomeric polymers, such as silicones (e.g., polysiloxanes and substituted polysiloxanes), polyurethanes, thermoplastic elastomers, ethylene vinyl acetate copolymers, polyolefin elastomers, and EPDM rubbers. Because of the elastic characteristics of these polymers, when these polymers are included as an intermediate layer, adherence of the drug-containing coating layer to the surface of the intermediate layer and ultimately to the medical device may increase when the medical device is subjected to forces or stress The intermediate layer may also comprise one or more of the additives previously described, or other components, in order to maintain the integrity and adherence of the drug-containing coating layer or layers to the medical device, to facilitate both adherence of drug and additive components during transit and rapid elution during deployment at the site of therapeutic intervention, to increase retention of the therapeutic agent in tissue, or combinations of these benefits.

The intermediate layer 40 may also facilitate the manufacture of the balloon 12. For example, the application of the intermediate layer 40 may change the surface energy of the surface of a bare balloon by providing a more consistent, conformal layer onto which the drug coating layer 30 may be applied. A more consistent, conformal surface is less likely to collect foreign matter during manufacturing.

Drug Coating Layer Therapeutic Agent

The drug coating layer 30 of the medical device according to embodiments includes a therapeutic agent and at least one additive.

In embodiments of the present disclosure, the therapeutic agent or substance may include drugs or biologically active materials. The drugs can be of various physical states, e.g., molecular distribution, crystal forms or cluster forms. Examples of drugs that are especially useful in embodiments of the present disclosure are lipophilic, hydrophobic, and substantially water insoluble drugs. Further examples of drugs may include paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature.

Other drugs that may be useful in embodiments of the present disclosure include, without limitation, glucocorticoids (e.g., dexamethasone, betamethasone), hirudin, angiopeptin, aspirin, growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents.

Also useful in embodiments of the present disclosure are polynucleotides, antisense, RNAi, or siRNA, for example, that inhibit inflammation and/or smooth muscle cell or fibroblast proliferation, contractility, or mobility.

Anti-platelet agents can include drugs such as aspirin and dipyridamole. Aspirin is classified as an analgesic, anti-pyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present disclosure can include drugs such as heparin, protamine, hirudin and tick anticoagulant protein. Anti-oxidant agents can include probucol. Anti-proliferative agents can include drugs such as amlodipine and doxazosin. Anti-mitotic agents and anti-metabolite agents that can be used in embodiments of the present disclosure include drugs such as methotrexate, azathioprine, vincristine, vinblastine, 5-fluorouracil, adriamycin, and mutamycin. Antibiotic agents for use in embodiments of the present disclosure include penicillin, cefoxitin, oxacillin, tobramycin, and gentamicin. Suitable antioxidants for use in embodiments of the present disclosure include probucol. Additionally, genes or nucleic acids, or portions thereof can be used as the therapeutic agent in embodiments of the present disclosure. Furthermore, collagen-synthesis inhibitors, such as tranilast, can be used as a therapeutic agent in embodiments of the present disclosure.

Photosensitizing agents for photodynamic or radiation therapy, including various porphyrin compounds such as porfimer, for example, are also useful as drugs in embodiments of the present disclosure.

Drugs for use in embodiments of the present disclosure also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, .beta.-sitosterin, ademetionine, myrtecaine, polidocanol, nonivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon a, .beta. and y, histamine antagonists, serotonin blockers, apoptosis inhibitors, apoptosis regulators such as p65 NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecainide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxysorospermin, psychorubin, ricin A, sanguinarine, manwu wheat acid, methylsorbifolin, spatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present disclosure. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations may reduce complications from using a high dose of the drug.

As used herein, "derivative" refers to a chemically or biologically modified version of a chemical compound that is structurally similar to a parent compound and (actually or theoretically) derivable from that parent compound. A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives which can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115; Design of Prodrugs, H. Bundgaard (ed.), Elsevier, 1985; or H. Bundgaard, Drugs of the Future 16 (1991) 443. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form alkali metal salts or alkaline earth metal salts (e.g., sodium salts, potassium salts, magnesium salts and calcium salts, as well as salts with physiologically tolerable quaternary ammonium ions and acid addition salts with ammonia and physiologically tolerable organic amines such as triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, "analog" or "analogue" refers to a chemical compound that is structurally similar to another but differs slightly in composition (as in the replacement of one atom by an atom of a different element or in the presence of a particular functional group), but may or may not be derivable from the parent compound. A "derivative" differs from an "analog" or "analogue" in that a parent compound may be the starting material to generate a "derivative," whereas the parent compound may not necessarily be used as the starting material to generate an "analog."

Numerous paclitaxel analogs are known in the art. Examples of paclitaxel include docetaxol (TAXOTERE, Merck Index entry 3458), and 3'-desphenyl-3'-(4-ntirophenyl)-N-debenzoyl-N-(t-butoxycarbonyl)-10-deacetyltaxol. Further representative examples of paclitaxel analogs that can be used as therapeutic agents include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di(sodium 1,2-benzenedicarboxylate, 10-desacetoxy-11,12-dihydrotaxol-10,12(18)-diene derivatives, 10-desacetoxytaxol, Protaxol (2'- and/or 7-O-ester derivatives), (2'- and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol), derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG(5000) carbamate taxol, 2'-benzoyl and 2',7-dibenzoyl taxol derivatives, other prodrugs (2'-acetyltaxol; 2',7-diacetyltaxol; 2'succinyltaxol; 2'-(beta-alanyl)-taxol); 2'gamma-aminobutyryltaxol formate; ethylene glycol derivatives of 2'-succinyltaxol; 2'-glutaryltaxol; 2'-(N,N-dimethylglycyl)taxol; 2'-(2-(N,N-dimethylamino)propionyl)taxol; 2'orthocarboxybenzoyl taxol; 2'aliphatic carboxylic acid derivatives of taxol, Prodrugs {2'(N,N-diethylaminopropionyl)taxol, 2'(N,N-dimethylglycyl)taxol, 7(N,N-dimethylglycyl)taxol, 2',7-di-(N,N-dimethylglycyl)taxol, 7(N,N-diethylaminopropionyl)taxol, 2',7-di(N,N-diethylaminopropionyl)taxol, 2'-(L-glycyl)taxol, 7-(L-glycyl)taxol, 2',7-di(L-glycyl)taxol, 2'-(L-alanyl)taxol, 7-(L-alanyl)taxol, 2',7-di(L-alanyl)taxol, 2'-(L-leucyl)taxol, 7-(L-leucyl)taxol, 2',7-di(L-leucyl)taxol, 2'-(L-isoleucyl)taxol, 7-(L-isoleucyl)taxol, 2',7-di(L-isoleucyl)taxol, 2'-(L-valyl)taxol, 7-(L-valyl)taxol, 2'7-di(L-valyl)taxol, 2'-(L-phenylalanyl)taxol, 7-(L-phenylalanyl)taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2',7-di(L-lysyl)taxol, 2'-(L-glutamyl)taxol, 7-(L-glutamyl) taxol, 2',7-di(L-glutamyl)taxol, 2'-(L-arginyl)taxol, 7-(L-arginyl)taxol, 2',7-di(L-arginyl)taxol, taxol analogues with modified phenylisoserine side chains, TAXOTERE, (N-debenzoyl-N-tert-(butoxycaronyl)-10-deacetyltaxol, and taxanes (e.g., baccatin III, cephalomannine, 10-deacetylbaccatin III, brevifoliol, yunantaxusin and taxusin); and other taxane analogues and derivatives, including 14-beta-hydroxy-10 deacetybaccatin III, debenzoyl-2-acyl paclitaxel derivatives, benzoate paclitaxel derivatives, phosphonooxy and carbonate paclitaxel derivatives, sulfonated 2'-acryloyl-taxol; sulfonated 2'-O-acyl acid paclitaxel derivatives, 18-site-substituted paclitaxel derivatives, chlorinated paclitaxel analogues, C4 methoxy ether paclitaxel derivatives, sulfenamide taxane derivatives, brominated paclitaxel analogues, Girard taxane derivatives, nitrophenyl paclitaxel, 10-deacetylated substituted paclitaxel derivatives, 14-beta-hydroxy-10 deacetylbaccatin III taxane derivatives, C7 taxane derivatives, C10 taxane derivatives, 2-debenzoyl-2-acyl taxane derivatives, 2-debenzoyl and -2-acyl paclitaxel derivatives, taxane and baccatin III analogues bearing new C2 and C4 functional groups, n-acyl paclitaxel analogues, 10-deacetylbaccatin III and 7-protected-10-deacetylbaccatin III derivatives from 10-deacetyl taxol A, 10-deacetyl taxol B, and 10-deacetyl taxol, benzoate derivatives of taxol, 2-aroyl-4-acyl paclitaxel analogues, ortho-ester paclitaxel analogues, 2-aroyl-4-acyl paclitaxel analogues and 1-deoxy paclitaxel and 1-deoxy paclitaxel analogues.

Other examples of paclitaxel analogs suitable for use herein include those listed in U.S. Pat. App. Pub. No. 2007/0212394, and U.S. Pat. No. 5,440,056, each of which is incorporated herein by reference.

Many rapamycin analogs are known in the art. Non-limiting examples of analogs of rapamycin include, but are not limited to, everolimus, tacrolimus, CCI-779, ABT-578, AP-23675, AP-23573, AP-23841, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, prerapamycin, temsirolimus, and 42-O-(2-hydroxy)ethyl rapamycin.

Other analogs of rapamycin include: rapamycin oximes (U.S. Pat. No. 5,446,048); rapamycin aminoesters (U.S. Pat. No. 5,130,307); rapamycin dialdehydes (U.S. Pat. No. 6,680,330); rapamycin 29-enols (U.S. Pat. No. 6,677,357); O-alkylated rapamycin derivatives (U.S. Pat. No. 6,440,990); water soluble rapamycin esters (U.S. Pat. No. 5,955,457); alkylated rapamycin derivatives (U.S. Pat. No. 5,922,730); rapamycin amidino carbamates (U.S. Pat. No. 5,637,590); biotin esters of rapamycin (U.S. Pat. No. 5,504,091); carbamates of rapamycin (U.S. Pat. No. 5,567,709); rapamycin hydroxyesters (U.S. Pat. No. 5,362,718); rapamycin 42-sulfonates and 42-(N-carbalkoxy)sulfamates (U.S. Pat. No. 5,346,893); rapamycin oxepane isomers (U.S. Pat. No. 5,344,833); imidazolidyl rapamycin derivatives (U.S. Pat. No. 5,310,903); rapamycin alkoxyesters (U.S. Pat. No. 5,233,036); rapamycin pyrazoles (U.S. Pat. No. 5,164,399); acyl derivatives of rapamycin (U.S. Pat. No. 4,316,885); reduction products of rapamycin (U.S. Pat. Nos. 5,102,876 and 5,138,051); rapamycin amide esters (U.S. Pat. No. 5,118,677); rapamycin fluorinated esters (U.S. Pat. No. 5,100,883); rapamycin acetals (U.S. Pat. No. 5,151,413); oxorapamycins (U.S. Pat. No. 6,399,625); and rapamycin silyl ethers (U.S. Pat. No. 5,120,842), each of which is specifically incorporated by reference.

Other analogs of rapamycin include those described in U.S. Pat. Nos. 7,560,457; 7,538,119; 7,476,678; 7,470,682; 7,455,853; 7,446,111; 7,445,916; 7,282,505; 7,279,562; 7,273,874; 7,268,144; 7,241,771; 7,220,755; 7,160,867; 6,329,386; RE37,421; 6,200,985; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; 5,023,262; all of which are incorporated herein by reference. Additional rapamycin analogs and derivatives can be found in the following U.S. Patent Application Pub. Nos., all of which are herein specifically incorporated by reference: 20080249123, 20080188511; 20080182867; 20080091008; 20080085880; 20080069797; 20070280992; 20070225313; 20070203172; 20070203171; 20070203170; 20070203169; 20070203168; 20070142423; 20060264453; and 20040010002.

In another embodiment, the hydrophobic therapeutic agent is provided as a total drug load in the drug coating layer 30. The total drug load of the hydrophobic therapeutic agent in the drug coating layer 30, in units of mass (μg) per unit area (mm$^2$) of the expandable balloon 12, may be from 1 μg/mm$^2$ to 20 μg/mm$^2$, or alternatively from 2 μg/mm$^2$ to 10 μg/mm$^2$, or alternatively from 2 μg/mm$^2$ to 6 μg/mm$^2$, or alternatively from 2.5 μg/mm$^2$ to 6 μg/mm$^2$. The hydrophobic therapeutic agent may also be uniformly distributed in the coating layer. Additionally, the hydrophobic therapeutic agent may be provided in a variety of physical states. For example, the hydrophobic therapeutic agent may be a molecular distribution, crystal form, or cluster form.

Drug Coating Layer Additives

In addition to the therapeutic agent or combination of therapeutic agents, the drug coating layer 30 of the medical devices according to embodiments includes at least one additive.

The additive of embodiments of the present disclosure has two parts. One part is hydrophilic and the other part is a drug affinity part. The drug affinity part is a hydrophobic part and/or has an affinity to the therapeutic agent by hydrogen bonding and/or van der Waals interactions. The drug affinity part of the additive may bind the lipophilic drug, such as rapamycin or paclitaxel. The hydrophilic portion accelerates diffusion and increases permeation of the drug into tissue. It may facilitate rapid movement of drug off the medical device during deployment at the target site by preventing hydrophobic drug molecules from clumping to each other and to the device, increasing drug solubility in interstitial spaces, and/or accelerating drug passage through polar head groups to the lipid bilayer of cell membranes of target tissues. The additives of embodiments of the present disclosure have two parts that function together to facilitate rapid release of drug off the device surface and uptake by target tissue during deployment (by accelerating drug contact with tissues for which drug has high affinity) while preventing the premature release of drug from the device surface prior to device deployment at the target site.

In embodiments of the present disclosure, the therapeutic agent is rapidly released after the medical device is brought into contact with tissue and is readily absorbed. For example, certain embodiments of devices of the present disclosure include drug coated balloon catheters that deliver a lipophilic anti-proliferative pharmaceutical (such as paclitaxel or rapamycin) to vascular tissue through brief, direct pressure contact at high drug concentration during balloon angioplasty. The lipophilic drug is preferentially retained in target tissue at the delivery site, where it inhibits hyperplasia and restenosis yet allows endothelialization. In these embodiments, coating formulations of the present disclosure not only facilitate rapid release of drug from the balloon surface and transfer of drug into target tissues during deployment, but also prevent drug from diffusing away from the device during transit through tortuous arterial anatomy prior to reaching the target site and from exploding off the device during the initial phase of balloon inflation, before the drug coating is pressed into direct contact with the surface of the vessel wall.

The additive according to certain embodiments has a drug affinity part and a hydrophilic part. The drug affinity part is a hydrophobic part and/or has an affinity to the therapeutic agent by hydrogen bonding and/or van der Waals interactions. The drug affinity part may include aliphatic and aromatic organic hydrocarbon compounds, such as benzene, toluene, and alkanes, among others. These parts are not water soluble. They may bind both hydrophobic drug, with which they share structural similarities, and lipids of cell membranes. They have no covalently bonded iodine. The drug affinity part may include functional groups that can form hydrogen bonds with drug and with itself. The hydrophilic part may include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others. One or more hydroxyl, carboxyl, acid, amide or amine groups, for example, may be advantageous since they easily displace water molecules that are hydrogen-bound to polar head groups and surface proteins of cell membranes and may function to remove this barrier between hydrophobic drug and cell membrane lipid. These parts can dissolve in water and polar solvents. These additives are not oils, lipids, or polymers. The therapeutic agent is not enclosed in micelles or liposomes or encapsulated in polymer particles. The additive of embodiments of the present disclosure has components to both bind drug and facilitate its rapid movement off the medical device during deployment and into target tissues.

The additives in embodiments of the present disclosure are surfactants and chemical compounds with one or more hydroxyl, amino, carbonyl, carboxyl, acid, amide or ester moieties. The surfactants include ionic, nonionic, aliphatic, and aromatic surfactants. The chemical compounds with one or more hydroxyl, amino, carbonyl, carboxyl, acid, amide or ester moieties are chosen from amino alcohols, hydroxyl carboxylic acid and anhydrides, ethyl oxide, ethyl glycols, amino acids, peptides, proteins, sugars, glucose, sucrose, sorbitan, glycerol, polyalcohol, phosphates, sulfates, organic acids, esters, salts, vitamins, and their substituted molecules.

As is well known in the art, the terms "hydrophilic" and "hydrophobic" are relative terms. To function as an additive in exemplary embodiments of the present disclosure, the compound includes polar or charged hydrophilic moieties as well as non-polar hydrophobic (lipophilic) moieties.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute]octanol/[solute]water). Compounds with higher log Ps are more hydrophobic, while compounds with lower log Ps are more hydrophilic. Lipinski's rule suggests that pharmaceutical compounds having log P<5 are typically more membrane permeable. For purposes of certain embodiments of the present disclosure, it is preferable that the additive has log P less than log P of the drug to be formulated (as an example, log P of paclitaxel is 7.4). A greater log P difference between the drug and the additive can facilitate phase separation of drug. For example, if log P of the additive is much lower than log P of the drug, the additive may accelerate the release of drug in an aqueous environment from the surface of a device to which drug might otherwise tightly adhere, thereby accelerating drug delivery to tissue during brief deployment at the site of intervention. In certain embodiments of the present disclosure, log P of the additive is negative. In other embodiments, log P of the additive is less than log P of the drug. While a compound's octanol-water partition coefficient P or log P is useful as a measurement of relative hydrophilicity and hydrophobicity, it is merely a rough guide that may be useful in defining suitable additives for use in embodiments of the present disclosure.

Suitable additives that can be used in embodiments of the present disclosure include, without limitation, organic and inorganic pharmaceutical excipients, natural products and derivatives thereof (such as sugars, vitamins, amino acids, peptides, proteins, and fatty acids), low molecular weight oligomers, surfactants (anionic, cationic, non-ionic, and ionic), and mixtures thereof. The following detailed list of additives useful in the present disclosure is provided for exemplary purposes only and is not intended to be comprehensive. Many other additives may be useful for purposes of the present disclosure.

Surfactants

The surfactant can be any surfactant suitable for use in pharmaceutical compositions. Such surfactants can be anionic, cationic, zwitterionic or non-ionic. Mixtures of surfactants are also within the scope of the disclosure, as are combinations of surfactant and other additives. Surfactants often have one or more long aliphatic chains such as fatty acids that may insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. In certain embodiments of the present disclosure, a higher HLB value is preferred, since increased hydrophilicity may facilitate release of hydrophobic drug from the surface of the device. In one embodiment, the HLB of the surfactant additive is higher than 10. In another embodiment, the additive HLB is higher than 14. Alternatively, surfactants having lower HLB may be preferred when used to prevent drug loss prior to device deployment at the target site, for example in a top coat over a drug layer that has a very hydrophilic additive. The HLB values of surfactant additives in certain embodiments are in the range of 0.0-40.

It should be understood that the HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants may be identified that have suitable hydrophilicity or hydrophobicity for use in embodiments of the present disclosure, as described herein.

PEG-Fatty Acids and PEG-Fatty Acid Mono and Diesters

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid, myristoleic acid, palmitoleic acid, linoleic acid, linolenic acid, eicosapentaenoic acid, erucic acid, ricinoleic acid, and docosahexaenoic acid are most useful in embodiments of the present disclosure. Preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. PEG-15 12-hydroxystearate (Solutol HS 15) is a nonionic surfactant used in injection solutions. Solutol HS 15 is a preferable additive in certain embodiments of the disclosure since it is a white paste at room temperature that becomes a liquid at about 30° C., which is above room temperature but below body temperature. The HLB values are in the range of 4-20.

The additive (such as Solutol HS 15) is in paste, solid, or crystal state at room temperature and becomes liquid at body temperature. Certain additives that are liquid at room temperature may make the manufacturing of a uniformly coated medical device difficult. Certain liquid additives may hinder solvent evaporation or may not remain in place on the surface of the medical device during the process of coating a device, such as the balloon portion of a balloon catheter, at room temperature. In certain embodiments of the present disclosure, paste and solid additives are preferable since they can stay localized on the medical device as a uniform coating that can be dried at room temperature. In some embodiments, when the solid coating on the medical device is exposed to the higher physiologic temperature of about 37° C. during deployment in the human body, it becomes a liquid. In these embodiments, the liquid coating very easily releases from the surface of the medical device and easily transfers into the diseased tissue. Additives that have a temperature-induced state change under physiologic conditions are very important in certain embodiments of the disclosure, especially in certain drug coated balloon catheters. In certain embodiments, both the solid additive and the liquid additive are used in combination in the drug coatings of the disclosure. The combination improves the integrity of the coatings for medical devices. In certain embodiments of the present disclosure, at least one solid additive is used in the drug coating.

Polyethylene glycol fatty acid diesters are also suitable for use as surfactants in the compositions of embodiments of the present disclosure. Most preferred hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present disclosure, including mixtures of two or more commercial surfactants as well as mixtures of surfactants with another additive or additives. Several PEG-fatty acid esters are marketed commercially as mixtures or mono- and diesters.

Polyethylene Glycol Glycerol Fatty Acid Esters

Preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products

A large number of surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil, polyethylene glycol-glycerol ricinoleate (Incrocas-35, and Cremophor EL&ELP), PEG-40 hydrogenated castor oil (Cremophor RH 40), PEG-15 hydrogenated castor oil (Solutol HS 15), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® b M 2735 CS), PEG-8 corn oil (Labrafil® WL 2609 BS), PEG-20 corn glycerides (Crovol M40), and PEG-20 almond glycerides (Crovol A40).

Polyglyceryl Fatty Acids

Polyglycerol esters of fatty acids are also suitable surfactants for use in embodiments of the present disclosure. Among the polyglyceryl fatty acid esters, preferred hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Preferred hydrophilic surfactants include polyglyceryl-10 laurate (Nikkol Decaglyn 1-L), polyglyceryl-10 oleate (Nikkol Decaglyn 1-0), and polyglyceryl-10 mono, dioleate (Caprol® PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also preferred surfactants.

Propylene Glycol Fatty Acid Esters

Esters of propylene glycol and fatty acids are suitable surfactants for use in embodiments of the present disclosure. In this surfactant class, preferred hydrophobic surfactants include propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800).

Sterol and Sterol Derivatives

Sterols and derivatives of sterols are suitable surfactants for use in embodiments of the present disclosure. Preferred derivatives include the polyethylene glycol derivatives. A preferred surfactant in this class is PEG-24 cholesterol ether (Solulan C-24).

Polyethylene Glycol Sorbitan Fatty Acid Esters

A variety of PEG-sorbitan fatty acid esters are available and are suitable for use as surfactants in embodiments of the present disclosure. Among the PEG-sorbitan fatty acid esters, preferred surfactants include PEG-20 sorbitan monolaurate (Tween-20), PEG-4 sorbitan monolaurate (Tween-21), PEG-20 sorbitan monopalmitate (Tween-40), PEG-20 sorbitan monostearate (Tween-60), PEG-4 sorbitan monostearate (Tween-61), PEG-20 sorbitan monooleate (Tween-80), PEG-4 sorbitan monooleate (Tween-81), PEG-20 sorbitan trioleate (Tween-85). Laurate esters are preferred because they have a short lipid chain compared with oleate esters, increasing drug absorption.

Polyethylene Glycol Alkyl Ethers

Ethers of polyethylene glycol and alkyl alcohols are suitable surfactants for use in embodiments of the present disclosure. Preferred ethers include Lanethes (Laneth-5, Laneth-10, Laneth-15, Laneth-20, Laneth-25, and Laneth-40), laurethes (Laureth-5, laureth-10, Laureth-15, laureth-20, Laureth-25, and laureth-40), Olethes (Oleth-2, Oleth-5, Oleth-10, Oleth-12, Oleth-16, Oleth-20, and Oleth-25), Stearethes (Steareth-2, Steareth-7, Steareth-8, Steareth-10, Steareth-16, Steareth-20, Steareth-25, and Steareth-80), Cetethes (Ceteth-5, Ceteth-10, Ceteth-15, Ceteth-20, Ceteth-25, Ceteth-30, and Ceteth-40),PEG-3 oleyl ether (Volpo 3) and PEG-4 lauryl ether (Brij 30).

Sugars and Sugar Derivatives

Sugar derivatives are suitable surfactants for use in embodiments of the present disclosure. Preferred surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, and octyl-β-D-thioglucopyranoside.

Polyethylene Glycol Alkyl Phenols

Several PEG-alkyl phenol surfactants are available, such as PEG-10-100 nonyl phenol and PEG-15-100 octyl phenol ether, Tyloxapol, octoxynol, nonoxynol, and are suitable for use in embodiments of the present disclosure.

Polyoxyethylene-Polyoxypropylene (POE-POP) Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present disclosure. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula: HO $(C_2H_4O)_a(C_3H_6O)_b$ $(C_2H_4O)_aH$, where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Polyester-Polyethylene Glycol Block Copolymers

The polyethylene glycol-polyester block copolymers are a unique class of polymeric surfactants. The unique structure of the surfactants, with hydrophilic polyethylene glycol (PEG) and hydrophobic polyester moieties in well-defined ratios and positions, provides a wide variety of surfactants suitable for use in embodiments of the present disclosure. The polyesters in the block polymers include poly(L-lactide) (PLLA), poly(DL-lactide)(PDLLA), poly(D-lactide) (PDLA), polycaprolactone(PCL), polyesteramide(PEA), polyhydroxyalkanoates, polyhydroxybutyrate(PHB), polyhydroxybutyrate-co-hydroxyvalerates (PHBV), polyhydroxybutyrate-co-hydroxyhexanoate (PHBHx), polyaminoacids, polyglycolide or polyglycolic acid (PGA), polyglycolide and its copolymers (poly(lactic-co-glycolic acid) with lactic acid, poly(glycolide-co-caprolactone) with ε-caprolactone, and poly (glycolide-co-trimethylene carbonate) with trimethylene carbonate), and their copolyesters. Examples are PLA-b-PEG, PLLA-b-PEG, PLA-co-PGA-b-PEG, PCL-co-PLLA-b-PEG, PCL-co-PLLA-b-PEG, PEG-b-PLLA-b-PEG, PLLA-b-PEG-b-PLLA, PEG-b-PCL-b-PEG, and other di, tri and multiple block copolymers. The hydrophilic block can be other hydrophilic or water soluble polymers, such as polyvinylalcohol, polyvinylpyrrolidone, polyacrylamide, and polyacrylic acid.

Polyethylene Glycol Graft Copolymers

One example of the graft copolymers is Soluplus (BASF, German). The Soluplus is a polyvinyl caprolactam-polyvinyl acetate-polyethylene glycol graft copolymer. The copolymer is a solubilizer with an amphiphilic chemical structure, which is capable of solubilizing poorly soluble drugs, such as paclitaxel, rapamycin and their derivatives, in aqueous media. Molecular weight of the copolymer is in the range of 90,000-140 000 g/mol.

Polymers, copolymers, block copolymers, and graft copolymers with amphiphilic chemical structures are used as additives in the embodiments. The polymers with amphiphilic chemical structures are block or graft copolymers. There are multiple segments (at least two segments) of different repeated units in the copolymers. In some embodiments, one of the segments is more hydrophilic than other segments in the copolymers. Likewise, one of the segments is more hydrophobic than other segments in the copolymers. For example, the polyethylene glycol segment is more hydrophilic than polyvinyl caprolactam-polyvinyl acetate segments in Soluplus (BASF, German). The polyester segment is more hydrophobic than polyethylene glycol segment in polyethylene glycol-polyester block copolymers. PEG is more hydrophilic tha PLLA in PEG-PLLA. PCL is more hydrophobic than PEG in PEG-b-PCL-b-PEG. The hydrophilic segments are not limited to polyethylene glycol. Other water soluble polymers, such as soluble polyvinylpyrrolidone and polyvinyl alcohol, can form hydrophilic segments in the polymers with amphilic structure. The copolymers can be used in combination with other additives in the embodiments.

Sorbitan Fatty Acid Esters

Sorbitan esters of fatty acids are suitable surfactants for use in embodiments of the present disclosure. Among these esters, preferred hydrophobic surfactants include sorbitan monolaurate (Arlacel 20), sorbitan monopalmitate (Span-40), and sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). And second, when the pH increases so as to convert a fraction of the ascorbyl palmitate to a more soluble salt, such as sodium ascorbyl palmitate.

Ionic Surfactants

Ionic surfactants, including cationic, anionic and zwitterionic surfactants, are suitable hydrophilic surfactants for use in embodiments of the present disclosure.

Anionic surfactants are those that carry a negative charge on the hydrophilic part. The major classes of anionic surfactants used as additives in embodiments of the disclosure are those containing carboxylate, sulfate, and sulfonate ions. Preferable cations used in embodiments of the disclosure are sodium, calcium, magnesium, and zinc. The straight chain is typically a saturated or unsaturated C8-C18 aliphatic group. Anionic surfactants with carboxylate ions include aluminum stearate, sodium stearate, calcium stearate, magnesium stearate, zinc stearate, sodium, zinc, and potassium oleates, sodium stearyl fumarate, sodium lauroyl sarcosinate, and sodium myristoyl sarcosinate. Anionic surfactants with sulfate group include sodium lauryl sulfate, sodium dodecyl sulfate, mono-, di-, and triethanolamine lauryl sulfate, sodium lauryl ether sulfate, sodium cetostearyl sulfate, sodium cetearyl sulfate, sodium tetradecyl sulfate, sulfated castor oil, sodium cholesteryl sulfate, sodium tetradecyl sulfate, sodium myristyl sulfate, sodium octyl sulfate, other mid-chain branched or non-branched alkyl sulfates, and ammonium lauryl sulfate. Anionic surfactants with sulfonate group include sodium docusate, dioctyl sodium sulfosuccinate, sodium lauryl sulfoacetate, sodium alkyl benzene sulfonate, sodium dodecyl benzene sulfonate, diisobutyl sodium sulfosuccinate, diamyl sodium sulfosuccinate, di(2-ethylhexyl)sulfosuccinate, and bis(1-methylamyl) sodium sulfosuccinate.

The most common cationic surfactants used in embodiments of the disclosure are the quaternary ammonium compounds with the general formula $R_4N^+X^-$, where $X^-$ is usually chloride or bromide ion and each R independently is chosen from alkyl groups containing 8 to 18 carbon atoms. These types of surfactants are important pharmaceutically because of their bactericidal properties. The principal cationic surfactants used in pharmaceutical and medical device preparation in the disclosure are quaternary ammonium salts. The surfactants include cetrimide, cetrimonium bromide, benzalkonium chloride, benzethonium chloride, cetylpyridinium chloride, hexadecyltrimethyl ammonium chloride, stearalkonium chloride, lauralkonium chloride, tetradodecyl ammonium chloride, myristyl picolinium chloride, and dodecyl picolinium chloride. These surfactants may react with some of the therapeutical agents in the formulation or coating. The surfactants may be preferred if they do not react with the therapeutic al agent.

Zwitterionic or amphoteric surfactants include dodecyl betaine, cocoamidopropyl betaine, cocoampho clycinate, among others.

Preferred ionic surfactants include sodium lauryl sulfate, sodium dodecyl sulfate, sodium lauryl ether sulfate, sodium cetostearyl sulfate, sodium cetearyl sulfate, sodium tetradecyl sulfate, sulfated castor oil, sodium cholesteryl sulfate, sodium tetradecyl sulfate, sodium myristyl sulfate, sodium octyl sulfate, other mid-chain branched or non-branched alkyl sulfates, sodium docusate, dioctyl sodium sulfosuccinate, sodium lauryl sulfoacetate, sodium alkyl benzene sulfonate, sodium dodecyl benzene sulfonate, benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate. These quaternary ammonium salts are preferred additives. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents. The HLB values of these surfactants are typically in the range of 20-40, such as sodium dodecyl sulfate (SDS) which has HLB values of 38-40.

Some of the surfactants described herein are very stable under heating. They survive an ethylene oxide sterilization process. They do not react with drugs such as paclitaxel or rapamycin under the sterilization process. The hydroxyl, ester, amide groups are preferred because they are unlikely to react with drug, while amine and acid groups often do react with paclitaxel or rapamycin during sterilization. Furthermore, surfactant additives improve the integrity and quality of the coating layer, so that particles do not fall off during handling. When the surfactants described herein are formulated with paclitaxel, experimentally it protects drug from premature release during the device delivery process while facilitating rapid release and elution of paclitaxel during a very brief deployment time of 0.2 to 2 minutes at the target site. Drug absorption by tissues at the target site is unexpectedly high experimentally.

Chemical Compounds with One or More Hydroxyl, Amino, Carbonyl, Carboxyl, Acid, Amide or Ester Moieties The chemical compounds with one or more hydroxyl, amino, carbonyl, carboxyl, acid, amide or ester moieties include amino alcohols, hydroxyl carboxylic acid, ester, and anhydrides, hydroxyl ketone, hydroxyl lactone, hydroxyl ester, sugar phosphate, sugar sulfate, sugar alcohols, ethyl oxide, ethyl glycols, amino acids, peptides, proteins, sorbitan, glycerol, polyalcohol, phosphates, sulfates, organic acids, esters, salts, vitamins, combinations of amino alcohols and organic acids, and their substituted molecules. Hydrophilic chemical compounds with one or more hydroxyl, amino, carbonyl, carboxyl, acid, amide or ester moieties having a molecular weight less than 5,000-10,000 are preferred in certain embodiments. In other embodiments, molecular weight of the additive with one or more hydroxyl, amino, carbonyl, carboxyl, acid, amide, or ester moieties is preferably less than 1000-5,000, or more preferably less than 750-1,000, or most preferably less than 750. In these embodiments, the molecular weight of the additive is preferred to be less than that of the drug to be delivered.

Further, the molecular weight of the additive is preferred to be higher than 80 since molecules with molecular weight less than 80 very easily evaporate and do not stay in the coating of a medical device. If the additive is volatile or in liquid state at room temperature, it is important that its molecular weight be above 80 in order not to lose additive during evaporation of solvent in the coating process. However, in certain embodiments in which the additive is not volatile, such as the solid additives of alcohols, esters, amides, acids, amines and their derivatives, the molecular weight of the additive can be less than 80, less than 60, and less than 20 since the additive will not easily evaporate from the coating. The solid additives can be crystal, semicrystal, and amorphous. Small molecules can diffuse quickly. They can release themselves easily from the delivery balloon, accelerating release of drug, and they can diffuse away from drug when the drug binds tissue of the body lumen.

In certain embodiments, more than four hydroxyl groups are preferred, for example in the case of a high molecular weight additive. Large molecules diffuse slowly. If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. The hydroxyl group is preferred as the hydrophilic moiety because it is unlikely to react with water insoluble drug, such as paclitaxel or rapamycin.

In some embodiments, the chemical compound having more than four hydroxyl groups has a melting point of 120° C. or less. In some embodiments, the chemical compound having more than four hydroxyl groups has three adjacent hydroxyl groups that in stereo configuration are all on one side of the molecule. For example, sorbitol and xylitol have three adjacent hydroxyl groups that in stereoconfiguration are all on one side of the molecule, while galactitol does not. The difference impacts the physical properties of the isomers such as the melting temperature. The stereoconfiguration of the three adjacent hydroxyl groups may enhance drug binding. This will lead to improved compatibility of the water insoluble drug and hydrophilic additive, and improved tissue uptake and absorption of drug.

The chemical compounds with amide moieties are important to the coating formulations in certain embodiments of the disclosure. Urea is one of the chemical compounds with amide groups. Others include biuret, acetamide, lactic acid amide, aminoacid amide, acetaminophen, uric acid, polyurea, urethane, urea derivatives, niacinamide, N-methylacetamide, N,N-dimethylacetamide, sulfacetamide sodium, versetamide, lauric diethanolamide, lauric myristic diethanolamide, N,N-Bis(2-hydroxyethyl stearamide), cocamide MEA, cocamide DEA, arginine, and other organic acid amides and their derivatives. Some of the chemical compounds with amide groups also have one or more hydroxyl, amino, carbonyl, carboxyl, acid or ester moieties.

One of the chemical compounds with amide group is a soluble and low molecular weight povidone. The povidone includes Kollidon 12 PF, Kollidon 17 PF, Kollidon 17, Kollidon 25, and Kollidon 30. The Kollidon products consist of soluble and insoluble grades of polyvinylpyrrolidone of various molecular weights and particle sizes, a vinylpyrrolidone/vinyl acetate copolymer and blend of polyvinyl acetate and polyvinylpyrrolidone. The family products are entitled Povidone, Crospovidone and Copovidone. The low molecular weights and soluble Povidones and Copovidones are especially important additives in the embodiments. For example, Kollidon 12 PF, Kollidon 17 PF, and Kollidon 17 are very important. The solid povidone can keep integrity of the coating on the medical devices. The low molecular weight povidone can be absorbed or permeated into the diseased tissue. The preferred range of molecular weight of the povidone are less than 54000 Dalton, less than 11000 Dalton, less than 7000 Dalton, less than 4000. They can solublize the water insoluble thearepeutic agents. Due to these properties of solid, low molecular weight and tissue absorption/permeability, the Povidone and Copovidone are especially useful. The Povidone can be used in combinations with other additives. In one embodiment Povidone and a nonionic surfactant (such as PEG-15 12-hydroxystearate (Solutol HS 15), Tween 20, Tween 80, Cremophor RH40, Cremophor EL &ELP), can be formulated with paclitaxel or rapamycin or their analogue as a coating for medical devices, such as balloon catheters.

The chemical compounds with ester moieties are especially important to the coating formulations in certain embodiments. The products of organic acid and alcohol are the chemical compounds with ester groups. The chemical compounds with ester groups often are used as plasticers for polymeric materials. The wide variety of ester chemical compounds includes sebates, adipates, gluterates, and phthalates. The examples of these chemical compounds are bis (2-ethylhexyl) phthalate, di-n-hexyl phthalate, diethyl phthalate, bis (2-ethylhexyl) adipate, dimethyl adipate, dioctyl adipate, dibutyl sebacate, dibutyl maleate, triethyl citrate, acetyl triethyl citrate, trioctyl citrate, trihexyl citrate, butyryl trihexyl citrate, and trimethyl citrate.

Some of the chemical compounds with one or more hydroxyl, amine, carbonyl, carboxyl, amide or ester moieties described herein are very stable under heating. They survive an ethylene oxide sterilization process and do not react with the water insoluble drug paclitaxel or rapamycin during sterilization. L-ascorbic acid and its salt and diethanolamine, on the other hand, do not necessarily survive such a sterilization process, and they react with paclitaxel. A different sterilization method is therefore preferred for L-ascorbic acid and diethanolamine. Hydroxyl, ester, and amide groups are preferred because they are unlikely to react with therapeutic agents such as paclitaxel or rapamycin. Sometimes, amine and acid groups do react with paclitaxel, for example, experimentally, benzoic acid, gentisic acid, diethanolamine, and ascorbic acid were not stable under ethylene oxide sterilization, heating, and aging process and reacted with paclitaxel.

When the chemical compounds described herein are formulated with paclitaxel, a top coat layer may be advantageous in order to prevent premature drug loss during the device delivery process before deployment at the target site, since hydrophilic small molecules sometimes release drug too easily. The chemical compounds herein rapidly elute drug off the balloon during deployment at the target site. Surprisingly, even though some drug is lost during transit of the device to the target site when the coating contains these additives, experimentally drug absorption by tissue is unexpectedly high after only 0.2-2 minutes of deployment, for example, with the additive hydroxyl lactones such as ribonic acid lactone and gluconolactone.

Antioxidants

An antioxidant is a molecule capable of slowing or preventing the oxidation of other molecules. Oxidation reactions can produce free radicals, which start chain reactions and may cause degradiation of sensitive therapeutic agents, for example of rapamycin and its derivitives. Antioxidants terminate these chain reactions by removing free redicals, and they further inhibit oxidation of the active agent by being oxidized themselves. Antioxidants are used as an additive in certain embodiments to prevent or slow the oxidation of the therapeutic agents in the coatings for medical devices. Antioxidants are a type of free radical scavengers. The antioxidant is used alone or in combination with other additives in certain embodiments and may prevent degradation of the active therapeutic agent during sterilization or storage prior to use.

Some representative examples of antioxidants that may be used in the methods of the present disclosure include, without limitation, oligomeric or polymeric proanthocyanidins, polyphenols, polyphosphates, polyazomethine, high sulfate agar oligomers, chitooligosaccharides obtained by partial chitosan hydrolysis, polyfunctional oligomeric thioethers with sterically hindered phenols, hindered amines such as, without limitation, p-phenylene diamine, trimethyl dihydroquinolones, and alkylated diphenyl amines, substituted phenolic compounds with one or more bulky functional groups (hindered phenols) such as tertiary butyl, arylamines, phosphites, hydroxylamines, and benzofuranones. Also, aromatic amines such as p-phenylenediamine, diphenylamine, and N,N' disubstituted p-phenylene diamines may be utilized as free radical scavengers.

Other examples include, without limitation, butylated hydroxytoluene ("BHT"), butylated hydroxyanisole ("BHA"), L-ascorbate (Vitamin C), Vitamin E, herbal rosemary, sage extracts, glutathione, resveratrol, ethoxyquin, rosmanol, isorosmanol, rosmaridiphenol, propyl gallate, gallic acid, caffeic acid, p-coumeric acid, p-hydroxy benzoic acid, astaxanthin, ferulic acid, dehydrozingerone, chlorogenic acid, ellagic acid, propyl paraben, sinapic acid, daidzin, glycitin, genistin, daidzein, glycitein, genistein, isoflavones, and tertbutylhydroquinone. Examples of some phosphites include di(stearyl)pentaerythritol diphosphite, tris(2,4-di-tert.butyl phenyl)phosphite, dilauryl thiodipropionate and bis(2,4-di-tert.butyl phenyl)pentaerythritol diphosphite. Some examples, without limitation, of hindered phenols include octadecyl-3,5,di-tert.butyl-4-hydroxy cinnamate, tetrakis-methylene-3-(3',5'-di-tert.butyl-4-hydroxyphenyl)propionate methane 2,5-di-tert-butylhydroquinone, ionol, pyrogallol, retinol, and octadecyl-3-(3,5-di-tert.butyl-4-hydroxyphenyl)propionate. An antioxidants may include glutathione, lipoic acid, melatonin, tocopherols, tocotrienols, thiols, Beta-carotene, retinoic acid, cryptoxanthin, 2,6-di-tert-butylphenol, propyl gallate, catechin, catechin gallate, and quercetin. Preferable antioxidants are butylated hydroxytoluene(BHT) and butylated hydroxyanisole(BHA).

Fat-Soluble Vitamins and Salts Thereof

Vitamins A, D, E and K in many of their various forms and provitamin forms are considered as fat-soluble vitamins and in addition to these a number of other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present disclosure.

The following examples of fat-soluble vitamin derivatives and/or sources are also useful as additives: Alpha-tocopherol, beta-tocopherol, gamma-tocopherol, delta-tocopherol, tocopherol acetate, ergosterol, 1-alpha-hydroxycholecalciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). Folic acid is also of this type, and although it is water-soluble at physiological pH, it can be formulated in the free acid form. Other derivatives of fat-soluble vitamins useful in embodiments of the present disclosure may easily be obtained via well known chemical reactions with hydrophilic molecules.

Water-Soluble Vitamins and their Amphiphilic Derivatives

Vitamins B, C, U, pantothenic acid, folic acid, and some of the menadione-related vitamins/provitamins in many of their various forms are considered water-soluble vitamins. These may also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present disclosure. Salts of these can also be useful as additives in the present disclosure. Examples of water-soluble vitamins and derivatives include, without limitation, acetiamine, benfotiamine, pantothenic acid, cetotiamine, cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present disclosure. The linkage of a palmitate chain to vitamin C yields ascorbyl palmitate.

Amino Acids and Their Salts

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are other useful additives in embodiments of the disclosure.

Certain amino acids, in their zwitterionic form and/or in a salt form with a monovalent or multivalent ion, have polar groups, relatively high octanol-water partition coefficients, and are useful in embodiments of the present disclosure. In the context of the present disclosure we take "low-solubility amino acid" to mean an amino acid which has a solubility in unbuffered water of less than about 4% (40 mg/ml). These include Cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well known in the art hydrophilic molecules may be joined to hydrophobic amino acids, or hydrophobic molecules to hydrophilic amino acids, to make additional additives useful in embodiments of the present disclosure.

Catecholamines, such as dopamine, levodopa, carbidopa, and DOPA, are also useful as additives.

Oligopeptides, Peptides and Proteins

Oligopeptides and peptides are useful as additives, since hydrophobic and hydrophilic amino acids may be easily coupled and various sequences of amino acids may be tested to maximally facilitate permeation of tissue by drug.

Proteins are also useful as additives in embodiments of the present disclosure. Serum albumin, for example, is a particularly preferred additive since it is water-soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human intravascular use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and Their Esters, Amides and Anhydrides

Examples are acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, aleuritic acid, shellolic acid, and 2-pyrrolidone. Aleuritic acid and shellolic acid can form a resin called Shellac. The paclitaxel, aleuritic acid, and shellolic acid in combinations can be used as a drug releasing coating for balloon catheters.

These esters and anhydrides are soluble in organic solvents such as ethanol, acetone, methylethylketone, ethylacetate. The water insoluble drugs can be dissolved in organic solvent with these esters, amides and anhydrides, then applied easily on to the medical device, then hydrolyzed under high pH conditions. The hydrolyzed anhydrides or esters are acids or alcohols, which are water soluble and can effectively carry the drugs off the device into the vessel walls.

Other Chemical Compounds with One or More Hydroxyl, Amine, Carbonyl, Carboxyl, Amides or Ester Moieties The additives according to embodiments include amino alcohols, alcohols, amines, acids, amides and hydroxyl acids in both cyclo and linear aliphatic and aromatic groups. Examples are L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sugar alcohols, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of polyethylene glycol and polypropylene glycol, and derivatives and combinations thereof.

Combinations of Additives

Combinations of additives are also useful for purposes of the present disclosure.

One embodiment comprises the combination or mixture of two additives, for example, a first additive comprising a surfactant and a second additive comprising a chemical compound with one or more hydroxyl, amine, carbonyl, carboxyl, amides or ester moieties.

The combination or mixture of the surfactant and the small water-soluble molecule (the chemical compounds with one or more hydroxyl, amine, carbonyl, carboxyl, amides or ester moieties) has advantages. Formulations comprising mixtures of the two additives with water-insoluble drug are in certain cases superior to mixtures including either additive alone. The hydrophobic drugs bind extremely water-soluble small molecules more poorly than they do surfactants. They are often phase separated from the small water-soluble molecules, which can lead to suboptimal coating uniformity and integrity. The water-insoluble drug has Log P higher than both that of the surfactant and that of small water-soluble molecules. However, Log P of the surfactant is typically higher than Log P of the chemical compounds with one or more hydroxyl, amine, carbonyl, carboxyl, amides or ester moieties. The surfactant has a relatively high Log P (usually above 0) and the water soluble molecules have low Log P (usually below 0).

Some surfactants, when used as additives in embodiments of the present disclosure, adhere so strongly to the water-insoluble drug and the surface of the medical device that drug is not able to rapidly release from the surface of the medical device at the target site. On the other hand, some of the water-soluble small molecules (with one or more hydroxyl, amine, carbonyl, carboxyl, amides or ester moieties) adhere so poorly to the medical device that they release drug before it reaches the target site, for example, into serum during the transit of a coated balloon catheter to the site targeted for intervention. Suprisingly, by adjusting the ratio of the concentrations of the small hydrophilic molecule and the surfactant in the formulation, the inventor has found that the coating stability during transit and rapid drug release when inflated and pressed against tissues of the lumen wall at the target site of therapeutic intervention in certain cases is superior to a formulation comprising either additive alone. Furthermore, the miscibility and compatibility of the water-insoluble drug and the highly water-soluble molecules is improved by the presence of the surfactant. The surfactant also improves coating uniformity and integrity by its good adhesion to the drug and the small molecules. The long chain hydrophobic part of the surfactant binds drug tightly while the hydrophilic part of the surfactant binds the water-soluble small molecules.

The surfactants in the mixture or the combination include all of the surfactants described herein for use in embodiments of the disclosure. The surfactant in the mixture may be chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, Tween 20, Tween 40, Tween 60, p-isononylphenoxypolyglycidol, PEG laurate, PEG oleate, PEG stearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, polyglyceryl-6 oleate, polyglyceryl-6 myristate, polyglyceryl-6 palmitate, polyglyceryl-10 laurate, polyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, Tween 20, Tween 40, Tween 60, Tween 80, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside and their derivatives.

The chemical compound with one or more hydroxyl, amine, carbonyl, carboxyl, or ester moieties in the mixture or the combination include all of the chemical compounds with one or more hydroxyl, amine, carbonyl, carboxyl, or ester moieties described herein for use in embodiments of the disclosure. The chemical compound with one or more hydroxyl, amine, carbonyl, carboxyl, amide or ester moieties in the mixture has at least one hydroxyl group in one of the embodiments of this disclosure. In certain embodiments, more than four hydroxyl groups are preferred, for example in the case of a high molecular weight additive. In some embodiments, the chemical compound having more than four hydroxyl groups has a melting point of 120° C. or less. Large molecules diffuse slowly.

If the molecular weight of the additive or the chemical compound is high, for example if the molecular weight is above 800, above 1000, above 1200, above 1500, or above 2000; large molecules may elute off of the surface of the medical device too slowly to release drug under 2 minutes. If these large molecules contain more than four hydroxyl groups they have increased hydrophilic properties, which is necessary for relatively large molecules to release drug quickly. The increased hydrophilicity helps elute the coating off the balloon, accelerates release of drug, and improves or facilitates drug movement through water barrier and polar head groups of lipid bilayers to penetrate tissues. The hydroxyl group is preferred as the hydrophilic moiety because it is unlikely to react with water insoluble drug, such as paclitaxel or rapamycin.

The chemical compound with one or more hydroxyl, amine, carbonyl, carboxyl, amide or ester moieties in the mixture is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof.

Mixtures or combinations of a surfactant and a water-soluble small molecule confer the advantages of both additives. The water insoluble drug often has a poor compatibility with highly water-soluble chemical compounds, and the surfactant improves compatibility. The surfactant also improves the coating quality, uniformity, and integrity, and particles do not fall off the balloon during handling. The surfactant reduces drug loss during transit to a target site. The water-soluble chemical compound improves the release of drug off the balloon and absorption of the drug in the tissue. Experimentally, the combination was surprisingly effective at preventing drug release during transit and achieving high drug levels in tissue after very brief 0.2-2 minute deployment. Furthermore, in animal studies it effectively reduced arterial stenosis and late lumen loss.

Some of the mixtures or combinations of surfactants and water-soluble small molecules are very stable under heating. They survived an ethylene oxide sterilization process and do not react with the water insoluble drug paclitaxel or rapamycin during sterilization. The hydroxyl, ester, amide groups are preferred because they are unlikely to react with therapeutic agents such as paclitaxel or rapamycin. Sometimes amine and acid groups do react with paclitaxel and are not stable under ethylene oxide sterilization, heating, and aging. When the mixtures or combinations described herein are formulated with paclitaxel, a top coat layer may be advantageous in order to protect the drug layer and from premature drug loss during the device.

Liquid Additives

Solid additives are often used in the drug coated medical devices. Iopromide, an iodine contrast agent has been used with paclitaxel to coat balloon catheters. These types of coatings contain no liquid chemicals. The coating is an aggregation of paclitaxel solid and iopromide solid on the surface of the balloon catheters. The coating lacks adhesion to the medical device and the coating particles fall off during handling and interventional procedure. Water insoluble drugs are often solid chemicals, such as paclitaxel, rapamycin, and analogues thereof. In embodiments of the disclosure, a liquid additive can be used in the medical device coating to improve the integrity of the coating. It is preferable to have a liquid additive which can improve the compatibility of the solid drug and/or other solid additive. It is preferable to have a liquid additive which can form a solid coating solution, not aggregation of two or more solid particles. It is preferable to have at least one liquid additive when another additive and drug are solid.

The liquid additive used in embodiments of the present disclosure is not a solvent. The solvents such as ethanol, methanol, dimethylsulfoxide, and acetone, will be evaporated after the coating is dried. In other words, the solvent will not stay in the coating after the coating is dried. In contrast, the liquid additive in embodiments of the present disclosure will stay in the coating after the coating is dried. The liquid additive is liquid or semi-liquid at room temperature and one atmosphere pressure. The liquid additive may form a gel at room temperature. The liquid additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions. The liquid additive is not oil.

The non-ionic surfactants are often liquid additives. Examples of liquid additives include PEG-fatty acids and esters, PEG-oil transesterification products, polyglyceryl fatty acids and esters, Propylene glycol fatty acid esters, PEG sorbitan fatty acid esters, and PEG alkyl ethers as mentioned above. Some examples of a liquid additive are Tween 80, Tween 81, Tween 20, Tween 40, Tween 60, Solutol HS 15, Cremophor RH40, and Cremophor EL&ELP.

More Than One Additive

In one embodiment, the drug coating layer 30 and, optionally, the intermediate layer 40 (when present), includes more than one additive, for example, two, three, or four additives. In one embodiment, the drug coating layer 30 comprises at least one additive, the at least one additive comprises a first additive and a second additive, and the first additive is more hydrophilic than the second additive. In another embodiment, the drug coating layer 30 and, optionally, the intermediate layer 40 (when present) comprises at least one additive, the at least one additive comprises a first additive and a second additive, and the first additive has a different structure from that of the second additive. In another embodiment, the drug coating layer 30 and, optionally, the intermediate layer 40 (when present) comprises at least one additive, the at least one additive comprises a first additive and a second additive, and the HLB value of the first additive is higher than that of the second additive. In yet another embodiment, the drug coating layer 30 and, optionally, the intermediate layer 40 (when present), comprises at least one additive, the at least one additive comprises a first additive and a second additive, and the Log P value of first additive is lower than that of the second additive. For example, sorbitol (Log P −4.67) is more hydrophilic than Tween 20 (Log P about 3.0). PEG fatty ester is more hydrophilic than fatty acid. Butylated hydroxyanisole (BHA) (Log P 1.31) is more hydrophilic than butylated hydroxytoluene (BHT) (Log P 5.32). In one embodiment, the drug coating layer 30 and, optionally, the intermediate layer 40 (when present) comprises sorbitol and polysorbate 20 (Tween 20). In another embodiment, the drug coating layer 30 and, optionally, the intermediate layer 40 (when present) comprises pactilaxel, sorbitol and polysorbate 20 (Tween 20).

In another embodiment, the drug coating layer 30 and, optionally, the intermediate layer 40 (when present), comprises more than one surfactants, for example, two, three, or four surfactants. In one embodiment, the drug coating layer 30 and, optionally, the intermediate layer 40 (when present), comprises at least one surfactant, the at least one surfactant comprises a first surfactant and a second surfactant, and the first surfactant is more hydrophilic than the second surfactant. In another embodiment, the drug coating layer 30 and, optionally, the intermediate layer 40 (when present), comprises at least one surfactant, the at least one surfactant comprises a first surfactant and a second surfactant, and the HLB value of the first surfactant is higher than that of the second surfactant. For example, Tween 80 (HLB 15) is more hydrophilic than Tween 20 (HLB 16.7). Tween 80 (HLB 15) is more hydrophilic than Tween 81 (HLB 10). Pluronic F68 (HLB 29) is more hydrophilic than Solutol HS 15 (HLB 15.2). Sodium docecyl sulfate (HBL 40) is more hydrophilic than docusate sodium (HLB 10). Tween 80 (HBL 15) is more hydrophilic than Creamophor EL (HBL 13).

Preferred additives include p-isononylphenoxypolyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-nonyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); cetotiamine; cycothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, and derivatives and combinations thereof.(chemical compounds with one or more hydroxyl, amino, carbonyl, carboxyl, amide or ester moieties). Some of these additives are both water-soluble and organic solvent-soluble. They have good adhesive properties and adhere to the surface of polyamide medical devices, such as balloon catheters. They may therefore be used in the adherent layer, top layer, and/or in the drug layer of embodiments of the present disclosure. The aromatic and aliphatic groups increase the solubility of water insoluble drugs in the coating solution, and the polar groups of alcohols and acids accelerate drug permeation of tissue.

Other preferred additives according to embodiments of the disclosure include the combination or mixture or amide reaction products of an amino alcohol and an organic acid. Examples are lysine/glutamic acid, lysine acetate, lactobionic acid/meglumine, lactobionic acid/tromethanemine, lactobionic acid/diethanolamine, lactic acid/meglumine, lactic acid/tromethanemine, lactic acid/diethanolamine, gentisic acid/meglumine, gentisic acid/tromethanemine, gensitic acid/diethanolamine, vanillic acid/meglumine, vanillic acid/tromethanemine, vanillic acid/diethanolamine, benzoic acid/meglumine, benzoic acid/tromethanemine, benzoic acid/diethanolamine, acetic acid/meglumine, acetic acid/tromethanemine, and acetic acid/diethanolamine.

Other preferred additives according to embodiments of the disclosure include hydroxyl ketone, hydroxyl lactone, hydroxyl acid, hydroxyl ester, and hydroxyl amide. Examples are gluconolactone, D-glucoheptono-1,4-lactone, glucooctanoic lactone, gulonic acid lactone, mannoic lactone, erythronic acid lactone, ribonic acid lactone, glucuronic acid, gluconic acid, gentisic acid, lactobionic acid, lactic acid, acetaminophen, vanillic acid, sinapic acid, hydroxybenzoic acid, methyl paraben, propyl paraben, and derivatives thereof.

Other preferred additives that may be useful in embodiments of the present disclosure include riboflavin, riboflavin-phosphate sodium, Vitamin D3, folic acid (vitamin B9), vitamin 12, diethylenetriaminepentaacetic acid dianhydride, ethylenediaminetetraacetic dianhydride, maleic acid and anhydride, succinic acid and anhydride, diglycolic anhydride, glutaric anhydride, L-ascorbic acid, thiamine, nicotinamide, nicotinic acid, 2-pyrrolidone-5-carboxylic acid, cystine, tyrosine, tryptophan, leucine, isoleucine, phenylalanine, asparagine, aspartic acid, glutamic acid, and methionine.

From a structural point of view, these additives share structural similarities and are compatible with water insoluble drugs (such as paclitaxel and rapamycin). They often contain double bonds such as C=C, C=N, C=O in aromatic or aliphatic structures. These additives also contain amine, alcohol, ester, amide, anhydride, carboxylic acid, and/or hydroxyl groups. They may form hydrogen bonds and/or van der Waals interactions with drug. They are also useful in the top layer in the coating.

Compounds containing one or more hydroxyl, carboxyl, or amine groups, for example, are especially useful as additives since they facilitate drug release from the device surface and easily displace water next to the polar head groups and surface proteins of cell membranes and may thereby remove this barrier to hydrophobic drug permeability. They accelerate movement of a hydrophobic drug off the balloon to the lipid layer of cell membranes and tissues for which it has very high affinity. Such membranes and tissues may include those of the vascular system or other lumen within a human or veterinary patient such as the esophagus, trachea, colon, biliary tract, sinus passages, nasal passages, renal arteries, or urinary tract. They may also carry or accelerate the movement of drug off the balloon into more aqueous environments such as the interstitial space, for example, of vascular tissues that have been injured by balloon angioplasty or stent expansion.

Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic C=N groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for the vessel wall and can displace hydrogen-bound water molecules. At the same time, they have long chains of fatty acid, alcohol, ether and ester that can both complex with hydrophobic drug and integrate into the lipid structure of the cell membranes to form the part of the lipid structure. This deformation or loosening of the lipid membrane of target cells may further accelerate permeation of hydrophobic drug into tissue.

For another example, L-ascorbic acid, thiamine, maleic acids, niacinamide, and 2-pyrrolidone-5-carboxylic acid all have a very high water and ethanol solubility and a low molecular weight and small size. They also have structural components including aromatic C=N, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore preferably used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

In embodiments of the present disclosure, the additive is soluble in aqueous solvents and is soluble in organic solvents. Extremely hydrophobic compounds that lack sufficient hydrophilic parts and are insoluble in aqueous solvent, such as the dye Sudan Red, are not useful as additives in these embodiments. Sudan red is also genotoxic.

In one embodiment, the concentration density of the at least one therapeutic agent applied to the surface of the medical device is from about 1 to 20 µg/mm$^2$, or more preferably from about 2 to 6 µg/mm$^2$. In one embodiment, the concentration of the at least one additive applied to the surface of the medical device is from about 1 to 20 µg/mm$^2$. The ratio of additives to drug by weight in the coating layer in embodiments of the present disclosure is about 20 to 0.05, preferably about 10 to 0.5, or more preferably about 5 to 0.8.

The relative amount of the therapeutic agent and the additive in the coating layer may vary depending on applicable circumstances. The optimal amount of the additive can depend upon, for example, the particular therapeutic agent and additive selected, the critical micelle concentration of the surface modifier if it forms micelles, the hydrophilic-lipophilic-balance (HLB) of a surfactant or an additive's octonol-water partition coefficient (P), the melting point of the additive, the water solubility of the additive and/or therapeutic agent, the surface tension of water solutions of the surface modifier, etc.

The additives are present in exemplary coating compositions of embodiments of the present disclosure in amounts such that upon dilution with an aqueous solution, the carrier forms a clear, aqueous dispersion or emulsion or solution, containing the hydrophobic therapeutic agent in aqueous and organic solutions. When the relative amount of surfactant is too great, the resulting dispersion is visibly "cloudy".

The optical clarity of the aqueous dispersion can be measured using standard quantitative techniques for turbidity assessment. One convenient procedure to measure turbidity is to measure the amount of light of a given wavelength transmitted by the solution, using, for example, an UV-visible spectrophotometer. Using this measure, optical clarity corresponds to high transmittance, since cloudier solutions will scatter more of the incident radiation, resulting in lower transmittance measurements.

Another method of determining optical clarity and carrier diffusivity through the aqueous boundary layer is to quantitatively measure the size of the particles of which the dispersion is composed. These measurements can be performed on commercially available particle size analyzers.

Other considerations will further inform the choice of specific proportions of different additives. These considerations include the degree of bioacceptability of the additives and the desired dosage of hydrophobic therapeutic agent to be provided.

Solvents

Solvents for preparing of the coating layer may include, as examples, any combination of one or more of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/tetrahydrofuran. A preferred solvent in the top coat layer is acetone.

Organic solvents, such as short-chained alcohol, dioxane, tetrahydrofuran, dimethylformamide, acetonitrile, dimethylsulfoxide, etc., are particularly useful and preferred solvents in embodiments of the present disclosure because these organic solvents generally disrupt collodial aggregates and co-solubilize all the components in the coating solution.

The therapeutic agent and additive or additives may be dispersed in, solubilized, or otherwise mixed in the solvent. The weight percent of drug and additives in the solvent may be in the range of 0.1-80% by weight, preferably 2-20% by weight.

Another embodiment of the disclosure relates to a method for preparing a medical device, particularly, for example, a balloon catheter or a stent. First, a coating solution or suspension comprising at least one solvent, at least one therapeutic agent, and at least one additive is prepared. In at least one embodiment, the coating solution or suspension includes only these three components. The content of the therapeutic agent in the coating solution can be from 0.5-50% by weight based on the total weight of the solution. The content of the additive in the coating solution can be from 1-45% by weight, 1 to 40% by weight, or from 1-15% by weight based on the total weight of the solution. The amount of solvent used depends on the coating process and viscosity. It will affect the uniformity of the drug-additive coating but will be evaporated.

In other embodiments, two or more solvents, two or more therapeutic agents, and/or two or more additives may be used in the coating solution.

In other embodiments, a therapeutic agent, an additive and a polymeric material may be used in the coating solution, for example in a stent coating. In the coating, the therapeutic agent is not encapsulated in polymer particles.

Various techniques may be used for applying a coating solution to a medical device such as metering, casting, spinning, spraying, dipping (immersing), ink jet printing, electrostatic techniques, plasma etching, vapor deposition, and combinations of these processes. Choosing an application technique principally depends on the viscosity and surface tension of the solution. In embodiments of the present disclosure, metering, dipping and spraying are preferred because it makes it easier to control the uniformity of the thickness of the coating layer as well as the concentration of the therapeutic agent applied to the medical device. Regardless of whether the coating is applied by spraying or by dipping or by another method or combination of methods, each layer may be applied to the medical device in multiple application steps in order to control the uniformity and the amount of therapeutic substance and additive applied to the medical device.

Each applied layer is from about 0.1 µm to 15 µm in thickness. The total number of layers applied to the medical device is in a range of from about 2 to 50. The total thickness of the coating is from about 2 µm to 200 µm.

As discussed above, metering, spraying and dipping are particularly useful coating techniques for use in embodiments of the present disclosure. In a spraying technique, a coating solution or suspension of an embodiment of the present disclosure is prepared and then transferred to an application device for applying the coating solution or suspension to a balloon catheter.

An application device that may be used is a paint jar attached to an air brush, such as a Badger Model 150, supplied with a source of pressurized air through a regulator (Norgren, 0 to 160 psi). When using such an application device, once the brush hose is attached to the source of compressed air downstream of the regulator, the air is applied. The pressure is adjusted to approximately 15-25 psi and the nozzle condition checked by depressing the trigger.

Prior to spraying, both ends of the relaxed balloon are fastened to the fixture by two resilient retainers, i.e., alligator clips, and the distance between the clips is adjusted so that the balloon remained in a deflated, folded, or an inflated or partially inflated, unfolded condition. The rotor is then energized and the spin speed adjusted to the desired coating speed, about 40 rpm.

With the balloon rotating in a substantially horizontal plane, the spray nozzle is adjusted so that the distance from the nozzle to the balloon is about 1-4 inches. First, the coating solution is sprayed substantially horizontally with the brush being directed along the balloon from the distal end of the balloon to the proximal end and then from the proximal end to the distal end in a sweeping motion at a speed such that one spray cycle occurred in about three balloon rotations. The balloon is repeatedly sprayed with the coating solution, followed by drying, until an effective amount of the drug is deposited on the balloon.

In one embodiment of the present disclosure, the balloon is inflated or partially inflated, the coating solution is applied to the inflated balloon, for example by spraying, and then the balloon dried and subsequently deflated and folded. Drying may be performed under vacuum.

It should be understood that this description of an application device, fixture, and spraying technique is exemplary only. Any other suitable spraying or other technique may be used for coating the medical device, particularly for coating the balloon of a balloon catheter or stent delivery system or stent.

After the medical device is sprayed with the coating solution, the coated balloon is subjected to a drying in which the solvent in the coating solution is evaporated. This produces a coating matrix on the balloon containing the therapeutic agent. One example of a drying technique is placing a coated balloon into an oven at approximately 20° C. or higher for approximately 24 hours. Another example is air drying. Any other suitable method of drying the coating solution may be used. The time and temperature may vary with particular additives and therapeutic agents.

Optional Post Treatment

After depositing the drug-additive containing layer on the device of certain embodiments of the present disclosure, dimethyl sulfoxide (DMSO) or other solvent may be applied, by dip or spray or other method, to the finished surface of the coating. DMSO readily dissolves drugs and easily penetrates membranes and may enhance tissue absorption.

It is contemplated that the medical devices of embodiments of the present disclosure have applicability for treating blockages and occlusions of any body passageways, including, among others, the vasculature, including coronary, peripheral, and cerebral vasculature, the gastrointestinal tract, including the esophagus, stomach, small intestine, and colon, the pulmonary airways, including the trachea, bronchi, bronchioles, the sinus, the biliary tract, the urinary tract, prostate and brain passages. They are especially suited for treating tissue of the vasculature with, for example, a balloon catheter or a stent.

Yet another embodiment of the present disclosure relates to a method of treating a blood vessel. The method includes inserting a medical device comprising a coating into a blood vessel. The coating layer comprises a therapeutic agent and an additive. In this embodiment, the medical device can be configured as having at least an expandable portion. Some examples of such devices include balloon catheters, perfusion balloon catheters, an infusion catheter such as distal perforated drug infusion catheters, a perforated balloon, spaced double balloon, porous balloon, and weeping balloon, cutting balloon catheters, scoring balloon catheters, self-expanded and balloon expanded-stents, guide catheters, guide wires, embolic protection devices, and various imaging devices.

As mentioned above, one example of a medical device that is particularly useful in the present disclosure is a coated balloon catheter. A balloon catheter 10 typically has a long, narrow, hollow tube tabbed with a miniature, deflated balloon 12. In embodiments of the present disclosure, the balloon is coated with a drug solution. Then, the balloon is maneuvered through the cardiovascular system to the site of a blockage, occlusion, or other tissue requiring a therapeutic agent. Once in the proper position, the balloon is inflated and contacts the walls of the blood vessel and/or a blockage or occlusion. It is an object of embodiments of the present disclosure to rapidly and effectively/efficiently deliver drug to and facilitate absorption by target tissue. It is advantageous to efficiently deliver drug to tissue in as brief a period of time as possible while the device is deployed at the target site. The therapeutic agent is released into such tissue, for example the vessel walls, in about 0.1 to 30 minutes, for example, or preferably about 0.1 to 10 minutes, or more preferably about 0.2 to 2 minutes, or most preferably, about 0.1 to 1 minutes, of balloon inflation time pressing the drug coating into contact with diseased vascular tissue.

Given that a therapeutically effective amount of the drug can be delivered by embodiments of the present disclosure into, for example, the arterial wall, in some cases the need for a stent may be eliminated, obviating the complications of fracture and thrombosis associated therewith.

Should placement of a stent still be desired, a use for embodiments of the present disclosure is to crimp a stent, such as a bare metal stent (BMS), for example, over the drug coated balloon described in embodiments herein. When the balloon is inflated to deploy the stent at the site of diseased vasculature, an effective amount of drug is delivered into the arterial wall to prevent or decrease the severity of restenosis or other complications. Alternatively, the stent and balloon may be coated together, or the stent may be coated and then crimped on a balloon.

Further, the balloon catheter may be used to treat vascular tissue/disease alone or in combination with other methods for treating the vasculature, for example, photodynamic therapy or atherectomy. Atherectomy is a procedure to remove plaque from arteries. Specifically, atherectomy removes plaque from peripheral and coronary arteries. The medical device used for peripheral or coronary atherectomy may be a laser catheter or a catheter with rotating blades or sanding mechanisms or a direct atherectomy device on the end of a catheter. The catheter is inserted into the body and advanced through an artery to the area of narrowing. After the atherectomy has removed some of the plaque, balloon angioplasty using the coated balloon of embodiments of the present disclosure may be performed. In addition, stenting may be performed thereafter, or simultaneous with expansion of the coated balloon as described above. Photodynamic therapy is a procedure where light or irradiated energy is used to kill target cells in a patient. A light-activated photosensitizing drug may be delivered to specific areas of tissue by embodiments of the present disclosure. A targeted light or radiation source selectively activates the drug to produce a cytotoxic response and mediate a therapeutic anti-proliferative effect.

In some of the embodiments of drug-containing coatings and layers according to the present disclosure, the coating or layer does not include polymers, oils, or lipids. And, furthermore, the therapeutic agent is not encapsulated in polymer particles, micelles, or liposomes. As described above, such formulations have significant disadvantages and can inhibit the intended efficient, rapid release and tissue penetration of the agent, especially in the environment of diseased tissue of the vasculature.

Surface Modification by Application of Intermediate Layer

As previously described, the medical device such as a balloon catheter 10, for example, includes a modified exterior surface 25, namely, a surface that has been subjected to a surface modification that decreases a surface free energy of the exterior surface 25 before application of the drug coating layer 30. The surface modification may include application of an intermediate layer 40 on the exterior surface 25 before the drug coating layer 30 is applied. The application of the intermediate layer 40 may include plasma-polymerization of monomeric compounds to form the intermediate layer 40. Upon application of an intermediate layer 40 to an exterior surface of the medical device, the modified exterior surface 25 of the medical device includes the intermediate layer 40, and the drug coating layer 30 overlies the intermediate layer 40.

In some embodiments, the exterior surface of the medical device may be subjected initially to the fluorine plasma treatment, as previously described, followed by the plasma polymerization of an intermediate layer 40 on the exterior surface 25, followed by application of the drug coating layer 30. In some embodiments, the exterior surface may be subjected to the plasma-polymerization of the intermediate layer 40 on the exterior surface 25 without an initial fluorine plasma treatment, followed by application of the drug coating layer 30.

Without intent to be bound by theory, it is believed that increases of drug delivery to a target site, as well as prolonged uptake at the target site, may be facilitated by modifying both the particle sizes of the drug present in the drug coating layer and the electrostatic interactions of the drug in the drug coating layer with the surface of the medical device. Decreasing drug particle sizes alone can provide extended drug delivery, because for a given mass of drug, a larger total particle surface area available for contacting the target site is present when the particle size distribution is shifted to a greater fraction of smaller particles. The increased surface area may be counterbalanced, however, by increased electrostatic interaction of the smaller particles with the surface of the medical device. The increased electrostatic interaction may tend to hold the drug particles more tightly to the surface of the medical device. In turn, there is a need to optimize both the particle-size distribution of the drug in the drug coating layer and the electrostatic interaction of the drug particles with the exterior surface of the medical device. Surface modification through application of the intermediate layer on the exterior surface, according to embodiments, may address this particular need.

Surface energy of a substance results from cohesive interactions between atoms and molecules in the substance. The interactions include a dispersive component, a polar component, and a hydrogen bonding component. The dispersive component results from temporary fluctuations in charge distributions among the atoms or molecules including, for example, van der Waals interactions. The polar component results from permanent dipoles of individual atoms or molecules. The hydrogen bonding component results from atoms or molecules in a substance that are capable of forming hydrogen bonds with other atoms or molecules. The total surface energy of a substance equals the sum of the dispersive component, the polar component, and the hydrogen bonding component.

Interactions or adhesion between substances involve an interfacial tension related to the dispersive and polar components of the surface energies of the individual substances. The individual substances may include, for example, a substrate and a coating formulation overlying the substrate, or a substrate and a component of a coating formulation such as, for example, a drug particle. Adhesion between the two substances can to some extent be predicted through comparing the ratios of the dispersive and polar components of the individual substances. The closer the ratios are for the individual substances, the more interactions between the substances are to be expected and, thus, the greater the adhesion between the substances is to be expected. Substances that interact strongly with each other have a low interfacial tension.

Additionally, interactions between substrates and a coating formulation can be quantified according to Equation 1:

$$\text{Substrate Interaction} = \frac{(\sigma_{Polar} + \sigma_H)_{Formulation}}{(\sigma_{Polar} + \sigma_H)_{Substrate}} \quad \text{EQUATION 1}$$

In Equation 1, $\sigma_{polar}$ represents the polar component of surface energy and $\sigma_H$ represents the hydrogen bonding component of surface energy. Specific values for exemplary materials are provided in Table 1:

TABLE 1

| Material | $\sigma_{polar}$ | $\sigma_H$ | $\sigma_{polar} + \sigma_H$ |
|---|---|---|---|
| Nylon | 18.2 | 13.7 | 31.9 |
| Plasma-polymerized methylcyclohexane | 0 | 1 | 1 |
| Plasma-polymerized toluene | 1.4 | 2 | 3.4 |
| Plasma-polymerized xylene | 1 | 3.1 | 4.1 |
| Sample Formulation | 11.7 | 8.56 | 20.26 |

In Table 1, the Sample Formulation is a drug coating layer containing paclitaxel and two additives, according to one or more embodiments of this disclosure. Table 2 summarizes the expected interaction of the substrate with the Sample Formulation:

TABLE 2

| Substrate | Calculated Substrate Interaction with Sample Formulation |
|---|---|
| Nylon | 0.64 |
| Plasma-polymerized methylcyclohexane | 14.50 |
| Plasma-polymerized toluene | 5.94 |
| Plasma-polymerized xylene | 4.45 |

Without intent to be bound by theory, it is believed that the substrate interactions with a coating formulation may affect the morphology of the coating, the ability of the coating formulation to wet the substrate surface when the coating formulation is applied to the substrate surface, and the size distribution of drug particles in the coating formulation when the coating formulation dries after application to the substrate. For example, a larger substrate interaction may favor a shift in size distribution of drug particles in the drug coating layer toward smaller particles over larger particles. The shifted size distribution of drug particles, combined with the increased interaction of the substrate with the drug coating layer, may function synergistically to increase tissue retention of drug after periods such as 14 days, 28 days, or longer.

In one specific example, tissue retention at 14 days was compared between (1) a nylon balloon catheter coated with the Sample Formulation directly over the exterior surface of the balloon and (2) a nylon balloon catheter having a modified exterior surface comprising a parylene intermediate layer over the nylon balloon and a drug coating of the Sample Formulation over the intermediate layer. Particulate analysis of both balloons evidenced that the drug coating layer of the balloon (2) had an increased fraction of smaller drug particles and a decrease fraction of larger drug particles, compared to the drug coating layer on balloon (1). The tissue concentration of drug after the 14 days was determined to be approximately six times greater for the balloon for which the Sample Formulation was applied to the modified exterior surface than for the balloon for which the Sample Formulation was applied directly to the nylon balloon surface.

Surface Modification by Etching of Intermediate Layer

As previously described, the medical device such as a balloon catheter 10, for example, includes a modified exterior surface 25, namely, a surface that has been subjected to a surface modification that decreases a surface free energy of the exterior surface 25 before application of the drug coating layer 30. The surface modification may include plasma-polymerization of an intermediate layer 40 on the exterior surface 25 before the drug coating layer 30 is applied. Optionally, the surface modification may further include a fluorine plasma treatment, such as plasma fluorination, that implants a fluorine-containing species into the exterior surface 25 before the intermediate layer 40 and the drug coating layer 30 are applied. In embodiments, the modified exterior surface 25 may further include a plurality of depots or surface features formed by etching the intermediate layer 40 before the drug coating layer 30 is applied. The drug coating layer 30 may fill at least a portion of the depots or surface features.

Referring to FIGS. 3A-3C, the exterior surface 25 of the balloon 12 may be modified further, in addition to the application of the intermediate layer 40 by plasma polymerization, for example, by including a plurality of depots or surface features in the intermediate layer 40 before applying the drug coating layer 30. In FIG. 3A, the exterior surface 25 of the balloon 12 has been modified by application of the intermediate layer 40. The intermediate layer 40 may be a plasma polymerized layer, as previously described. The surface of the intermediate layer 40 is exposed to an etchant 80. The etchant may be a chemical etchant or a directed plasma, for example. In some embodiments, the etching may be carried out by first applying a photoresist material to the exterior surface 25, exposing the photoresist material to UV radiation through a photomask to selectively cure portions of the photoresist material, removing uncured photoresist material, etching the balloon, then removing the remaining photoresist. By way of further example, the intermediate layer 40 may be etched to form the plurality of recesses 21 and protrusions 23, or any other suitable pattern along the outer surface of the intermediate layer 40, by applying a pressurized medium thereon. For example, the pressurized medium may be oxygen, halogen plasma, a fluid, or other various imprinting means as will be apparent to those of ordinary skill in the art.

After the etching procedure, the intermediate layer 40 may include depots or other surface features. In the non-limiting illustrative embodiment of FIG. 3B, the depots or other surface features may include recesses 21 and protrustions 23, for example. In the embodiment of FIG. 3B, the recesses 21 and protrustions 23 are illustrated as channels essentially parallel to the longitudinal axis of the balloon catheter. In particular, the plurality of recesses 21 and protrusions 23 are disposed in an angular array about the exterior surface 25 (i.e. outer perimeter) of the balloon 12 extending parallel to a longitudinal length of the balloon 12. Each recess 21 of the plurality of recesses 21 is positioned between a pair of protrusions 23 along the intermediate layer 40. However, it should be understood that the depots or other surface features may have any desirable shape or configuration that may be produced on a balloon surface using customary etching techniques, with or without photolithography.

The outer surface of the intermediate layer 40 after the etching is no longer a planar surface. The nonplanar surface may facilitate the receipt and retention of the drug coating layer 30 in a manner that improves performance of the balloon catheter 10 by benefitting drug delivery and uptake characteristics. In the present example, the outer surface of the intermediate layer 40 is etched to form a profile including a pattern of a plurality of recesses 21 and a plurality of protrusions 23 positioned thereon.

Referring to FIG. 3C, the plurality of recesses 21 are sized, shaped, and configured to receive a portion of the drug coating layer 30 therein when the drug coating layer 30 is applied on the intermediate layer 40. A relatively lesser portion of the drug coating layer 30 is similarly received over the plurality of protrusions 23 in response to coating the intermediate layer 40 with the drug coating layer 30. The plurality of protrusions 23 are similarly sized, shaped and configured to retain the drug coating layer 30 within the plurality of recesses 21 as the balloon 12 of the balloon catheter 10 is inserted into a patient's body. In this instance, the plurality of protrusions 23 provide a raised surface for the intermediate layer 40 relative to the plurality of recesses 21 such that the portion of the drug coating layer 30 positioned within the plurality of recesses 21 is offset from an outermost-perimeter of the intermediate layer 40.

With a substantial portion of the drug coating layer 30 offset from outermost-surface of the intermediate layer 40, a substantial portion of the drug coating layer 30 is shielded from exposure to the surface shear forces generated along the outermost-surface as the balloon catheter 10 is advanced through a lumen in a patient's body. In particular, the plurality of recesses 21 may provide a depressed surface area for the drug coating layer 30 to reside as the balloon catheter 10 tranverses a bodily lumen to position the balloon 12 at a target treatment site, thereby minimizing the amount of the drug coating layer 30 that is displaced from the balloon 12 due to the shear stresses experienced by the balloon 12 along the outermost perimeter of the intermediate layer 40. In some embodiments, the bodily lumen may be a blood vessel. In other embodiments, the lumen may include any other lumen within a human or veterinary patient, such as within the esophagus, trachea, colon, biliary tract, sinus passages, nasal passages, renal arteries, or urinary tract.

As will be described in greater detail below, the drug coating layer 30 may be released from the plurality of recesses 21 in response to inflating the balloon catheter 10, because the plurality of recesses 21, and the drug coating layer 30 positioned therein, expand radially outwardly. In this instance, the shape and dimensions of the plurality of recesses 21 are modified (e.g., enlarged) thereby extending the portion of the drug coating layer 30 disposed within the plurality of recesses 21 radially outward and exposing the drug to tissue positioned adjacent to the balloon 12.

Although the intermediate layer 40 is shown as including a plurality of recesses 21 and protrusions 23 in the present example, it should be understood that various other patterns may be formed along the outer surface of the intermediate layer 40 to provide for the retention of the drug coating layer 30 thereon. It should be further understood that the plurality of recesses 21 and the plurality of protrusions 23 may vary in size and shape from adjacent recesses 21 and protrusions 23 along the outer surface of the intermediate layer 40, respectively.

As merely an illustrative example, the intermediate layer 40 may comprise a polymeric material such as a polyaromatic compound or a poly(p-xylylene) such as a parylene compound. For example, if the intermediate layer 40 is a parylene material, the presence of the intermediate layer 40 as the surface modification may affect the crystallinity of therapeutic agents such as paclitaxel, for example, in a manner that enhances the evaporation rate of drug coating layer 30 from the outer surface of the intermediate layer 40. The parylene composition of the intermediate layer 40 may generate smaller crystals of the therapeutic agent in the drug coating layer 30 once the drug coating layer 30 is overlaid over the intermediate layer 40, which thereby enhances the retention and/or adhesion of the drug coating layer 30 onto nearby tissue at the target treatment site when the drug coating layer 30 is released from the intermediate layer 40 and the balloon 12. By way of further example, the intermediate layer 40 may be etched to form the plurality of recesses 21 and protrusions 23, or any other suitable pattern along the outer surface of the intermediate layer 40, by applying a pressurized medium thereon. For example, the pressurized medium may be oxygen, halogen plasma, a fluid, or other various imprinting means as will be apparent to those of ordinary skill in the art.

In exemplary use, the intermediate layer 40 is evenly coated on the balloon 12 while the balloon 12 is inflated, so that the intermediate layer 40 may be equally applied along the exterior surface 25 of the balloon 12. With the intermediate layer 40 evenly distributed along the balloon 12, the plurality of recesses 21 and protrusions 23 may be integrally formed thereon by exposing the intermediate layer 40 to a pressurized medium prior to applying the drug coating layer 30. It should be understood that various other shapes, profiles, and patterns may be formed along an outer surface of the intermediate layer 40.

With the plurality of recesses 21 and protrusions 23 formed along the outer surface of the intermediate layer 40, the drug coating layer 30 may be applied. In this instance, with the balloon 12 maintained in the inflated state during application of the drug coating layer 30, the plurality of recesses 21 are radially expanded and facilitate the receipt of the drug coating layer 30 therein. As illustrated in FIG. 3C, after application of the drug coating layer 30, the plurality of protrusions 23 may encompass the portions of the drug coating layer 30 received within the plurality of recesses 21.

Without intent to be bound by theory, it is believed that as the drug coating layer 30 dries after being applied over the modified exterior surface 25 of the balloon 12 including the recesses 21 and protrusions 23, a more uniform drug coating layer 30 may form. In this instance, the balloon catheter 10 may be utilized for treating a target treatment site, for example, a blood vessel (not shown). As the balloon catheter 10 transverses through the blood vessel, the balloon 12 is exposed to the blood flowing therethrough such that the coated balloon experiences a shear force along the exterior surface in response to the blood flow moving through the blood vessel. With the drug coating layer 30 overlaid along the exterior surface 25 of the balloon 12, a portion of the drug coating layer 30 may be washed off by the shear force created by the blood traveling over balloon 12.

In particular, a variable amount of the therapeutic agent contained within the drug coating layer 30 is lost or dissolved prior to the balloon catheter 10 being positioned at the target treatment site to which the therapeutic agent is intended to be delivered. However, the lost amount of the drug coating layer 30 may be decreased by maintaining a substantial portion of the drug coating layer 30 within the plurality of recesses 21. The plurality of protrusions 23 provide a raised barrier surrounding the portion of drug coating layer 30 positioned within the plurality of recesses 21 such that a minimal amount of the drug coating layer 30 is exposed to the shear force of the blood flowing over the balloon 12. In contrast, the portion of the drug coating layer 30 received over the plurality of protrusions 23 is substantially exposed to the blood flowing through the blood vessel such that this portion of the drug coating layer 30 may be washed off as the balloon catheter 10 advances through blood vessel toward the target treatment site.

Once the balloon catheter 10 is positioned adjacent to the target treatment site, the balloon catheter 10 is inflated. The inflation expands the intermediate layer 40 that is overlies the modified exterior surface 25 of the balloon 12. As the intermediate layer 40 expands, the plurality of recesses 21 and protrusions 23 similarly extend outwardly such that the shape and dimensions of the plurality of recesses 21 and protrusions 23 increase (i.e. the surface area of intermediate layer 40 increases) thereby exposing the portion of the drug coating layer 30 disposed within the plurality of recesses 21 to the target treatment site. In particular, the remaining portion of the drug coating layer 30 maintained within the plurality of recesses 21 and along the plurality of protrusions 23 is extended radially outward with the inflation of the balloon 12 until physically encountering the nearby tissue at the target treatment site.

EXAMPLES

It should be understood that the following Examples are provided as illustrative only and are not intended to limit the scope of the disclosure. In general, the Examples herein demonstrate significant and unexpected improvements that result to medical devices having both the intermediate layer and the coating layer, compared to medical devices having only the coating layer. In all Examples, best efforts were made to keep procedural variables consistent.

The following abbreviations appear throughout the Examples:

Formula 1=a coating layer including paclitaxel as the therapeutic agent and a combination of a polysorbate (a PEG fatty ester) and a sugar alcohol as additives.
DCB=drug-coated balloon
PK=pharmacokinetic
PTA=percutaneous transluminal angioplasty Example 1

General Preparation and Testing of Devices

This Example describes the addition of a surface modification by application of an intermediate layer onto the base balloon material. An existing drug coating with the same drug coating process at the same dose density would be applied onto the base catheter with the added surface modification by application of an intermediate layer.

A surface modification by application of an intermediate layer is added directly onto the balloon material of a base PTA catheter. The manufacturing process of a balloon catheter with addition of the surface modification by application of an intermediate layer includes the following: (1) Assemble the base PTA catheter; (2) Apply surface modification by application of an intermediate layer and the drug-containing coating layer onto balloon surface; (3) Pleat and fold the balloon; (4) Apply the balloon protector; (5) Place in hoop and package, sterilize, and bulk package for shipment.

Step (2) in the previous paragraph may include the following steps: (1) The balloon area to be treated is exposed; (2) The catheter is optionally masked with exception of the balloon surface; (3) The balloon surface is optionally subjected to a pre-treatment process to clean and/or prepare the surface; (4) The masked or unmasked catheter is placed in the intermediate layer deposition chamber and the balloon surface is subjected to the treatment process for application of the surface modification; (5) the intermediate layer is treated, and the catheter is removed from the deposition chamber; (6) a drug-containing layer is deposited over the intermediate layer with the surface modification.

Example 2

Animal Study

Pharmacokinetics of modified drug-coating formulations and modified catheter platforms were studied in a swine arterial model. Drug coated balloons were coated using standard manufacturing processes. As a test group, semicompliant balloon catheters were coated first with a surface modification by application of an intermediate layer and subsequently with a Formula 1 drug coating formulation. Two surface modifications were tested: a xylene plasma polymerization surface modification and a methyl cyclohexane plasma polymerization surface modification. As a control group, semicompliant balloon catheters were coated with the Formula 1 layer without a surface modification. A total of eight vessel samples were treated and analyzed per group. Paclitaxel content analyses of tissue samples were performed by standard techniques.

The results of this study demonstrated an approximately 1.3-fold increase in drug uptake for the test group 1 (methyl cyclohexane plasma polymerization+Formula 1) as compared to the control at one hour. A 6.9-fold increase in drug retention was observed for the for the test group 1 (methyl cyclohexane plasma polymerization+Formula 1) as compared to the control group at 14 days. A 5.1-fold increase in drug retention was observed for the test group 2 (xylene plasma polymerization+Formula 1) as compared to the control group at 14 days.

In addition to the strict drug uptake measurements, an analysis of the percentage of drug retained in the tissue from 1 hour to 14 days. This was an approximation based on the values obtained in the 1 hour samples and the value obtained in the 14 day samples. Compared to the control, test group 1 (methyl cyclohexane plasma polymerization+Formula 1) was observed to have retained approximately 5.1 times as much paclitaxel from 1 hour to 14 days. Compared to the control, test group 2 (xylene plasma polymerization+Formula 1) was observed to have retained approximately 11.1 times as much paclitaxel from 1 hour to 14 days.

The invention claimed is:

1. A medical device comprising a coating layer applied overlying an intermediate layer that overlies a modified exterior surface of the medical device, wherein:
   the modified exterior surface comprises an exterior surface of the medical device subjected to a surface modification that decreases a surface free energy of the exterior surface before application of the coating layer;
   the intermediate layer comprises a plasma polymerized polymer; and
   the coating layer comprises a hydrophobic therapeutic agent and at least one additive, wherein the surface modification comprises a plasma fluorination that implants a fluorine-containing species into the exterior surface, whereby the modified exterior surface comprises at least one implanted fluorine species.

2. The medical device of claim 1, wherein the modified exterior surface further comprises a plurality of depots etched into the intermediate layer.

3. The medical device of claim 2, wherein the coating layer fills at least a portion of the depots.

4. The medical device of claim 1, wherein the intermediate layer is chosen from polymerized alkylcyclohexanes, polymerized toluene, polymerized xylenes, parylene C, parylene N, parylene D, parylene X, parylene AF-4, parylene SF, parylene HT, parylene VT-4 (parylene F), parylene CF, parylene A, and parylene AM, or combinations thereof.

5. The medical device of claim 2, wherein the intermediate layer is chosen from polymerized alkylcyclohexanes, polymerized toluene, polymerized xylenes, parylene C, parylene N, parylene D, parylene X, parylene AF-4, parylene SF, parylene HT, parylene VT-4 (parylene F), parylene CF, parylene A, and parylene AM, or combinations thereof.

6. The medical device of claim 1, wherein the therapeutic agent comprises paclitaxel, a paclitaxel analog or derivative, rapamycin, a rapamycin analog or derivative, or combinations thereof.

7. The medical device of claim 1, wherein the at least one additive comprises a polysorbate and a sugar alcohol.

8. The medical device of claim 1, wherein the medical device is a balloon catheter.

* * * * *